United States Patent
Cohen et al.

(10) Patent No.: US 7,295,881 B2
(45) Date of Patent: Nov. 13, 2007

(54) NERVE-BRANCH-SPECIFIC ACTION-POTENTIAL ACTIVATION, INHIBITION, AND MONITORING

(75) Inventors: Ehud Cohen, Ganei Tikva (IL); Tamir Ben-David, Tel Aviv (IL); Shai Ayal, Jerusalem (IL); Omry Ben-Ezra, Jerusalem (IL)

(73) Assignee: Biocontrol Medical Ltd., Yahud (IL)

( * ) Notice: Subject to any disclaimer, the term of this patent is extended or adjusted under 35 U.S.C. 154(b) by 321 days.

(21) Appl. No.: 10/745,514

(22) Filed: Dec. 29, 2003

(65) Prior Publication Data

US 2005/0149154 A1    Jul. 7, 2005

(51) Int. Cl.
*A61N 1/32* (2006.01)
(52) U.S. Cl. .......................... 607/118; 607/48
(58) Field of Classification Search ................ 607/118, 607/148, 46
See application file for complete search history.

(56) References Cited

U.S. PATENT DOCUMENTS

| | | | |
|---|---|---|---|
| 4,628,942 A | 12/1986 | Sweeney et al. | |
| 4,649,936 A | 3/1987 | Ungar et al. | |
| 5,755,750 A * | 5/1998 | Petruska et al. | 607/75 |
| 6,600,954 B2 | 7/2003 | Cohen et al. | |
| 2002/0099419 A1 * | 7/2002 | Cohen et al. | 607/46 |
| 2003/0045914 A1 | 3/2003 | Cohen et al. | |
| 2003/0050677 A1 | 3/2003 | Gross et al. | |
| 2004/0162594 A1 * | 8/2004 | King | 607/40 |

OTHER PUBLICATIONS

Rijkhoff et al. "Acute Animal Studies on the Use of An Anodal Block to Reduce Urethral Resistance in Sacral Root Stimulation", IEEE Transactions on Rehabilitation Engineering, 2(2): 92-98, 1994.

Fitzpatrick et al. "A Nerve Cuff Design for the Selective Activation and Blocking of Myelinated Nerve Fibres", Ann. Int. Conf. of the IEEE Engineering in Medicine and Biology Society, 13(2): 1991.

Jones et al., "Heart Rate Responses to Selective Stimulation of Cardiac Vagal C Fibres in Anaesthetized Cats, Rats and Rabbits", Journal of Physiology, 489(1): 203-214, 1995.

(Continued)

*Primary Examiner*—George R. Evanisko
*Assistant Examiner*—Michael Kahelin
(74) *Attorney, Agent, or Firm*—John P. White; Cooper & Dunham LLP

(57) ABSTRACT

A dual electrode arrangement, is provided, wherein two, preferably unidirectional, electrode configurations flank a nerve junction from which a preselected nerve branch issues, proximally and distally to the junction, with respect to the brain. The arrangement is conducive to the following: generating efferent action-potential propagations, substantially restricted to the preselected nerve branch, inhibiting afferent action-potential propagations, from the preselected nerve branch, selectively generating action-potential propagations, in a subset of nerve fibers of a predetermined diameter range, substantially restricted to the preselected nerve branch, and selectively inhibiting action-potential propagations, in a subset of nerve fibers of a predetermined diameter range, substantially restricted to the preselected nerve branch. The dual electrode arrangement is further conducive to monitoring naturally-occurring, efferent action-potential propagations, heading towards the preselected nerve branch, and monitoring naturally-occurring, afferent action-potential propagations, from the preselected nerve branch. The unidirectional electrode configurations may be monopolar, bipolar, tripolar, or multipolar. Communication with extracorporeal stations, and closed loop operations are also provided.

50 Claims, 15 Drawing Sheets

OTHER PUBLICATIONS

Rijkhoff et al. "Orderly Recruitment od Motoneurons in An Acute Rabbit Model", Proc. of the 20th Ann. Int. Conf. of the IEEE Engineering in Medicine and Biology Society, 20(5): 2564-2565, 1998.

Rattay "Analysis of Models for Extracellular Fiber Stimulation", IEEE Transactions on Biomedical Engineering, 36(7): 676-682, 1989.

Sweeney et al. "An Asymmetric Two Electrode Cuff for Generation of Unidirectionally Propagated Action Potentials", IEEE Transactions on Biomedical Engineering, BME-33(6): 541-549, 1986.

Van den Honert et al. "A Technique for Collision Block of Peripheral Nerve: Single Stimulus Analysis", IEEE Transactions on Biomedical Engineering, BME-28(5): 373-378, 1981.

Van den Honert et al. "Generation of Unidirectionally Propagated Action Potentials in A Peripheral Nerve by Brief Stimuli", Science, 206: 1311-1312, 1979.

Baratta et al. "Orderly Stimulation of Skeletal Muscle Motor Units With Tripolar Nerve Cuff Electrode", IEEE Transactions on Biomedical Engineering, 36(8): 836-843, 1989.

Ungar et al. "Generation of Unidirectionally Propagating Action Potentials Using A Monopolar Electrode Cuff", Annals of Biomedical Engineering, 14: 437-450, 1986. Abstract.

Tarler et al. "Selective and IndependantActivation Of Four Motor Fascicles Using A Four Contact Nerve-Cuff-Electrode", IEEE Transactions on Neutral Systems and Rehabilitation Engineering, 12(2): 251-257, 2004.

* cited by examiner

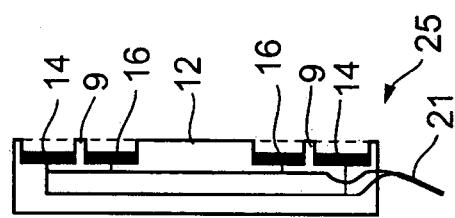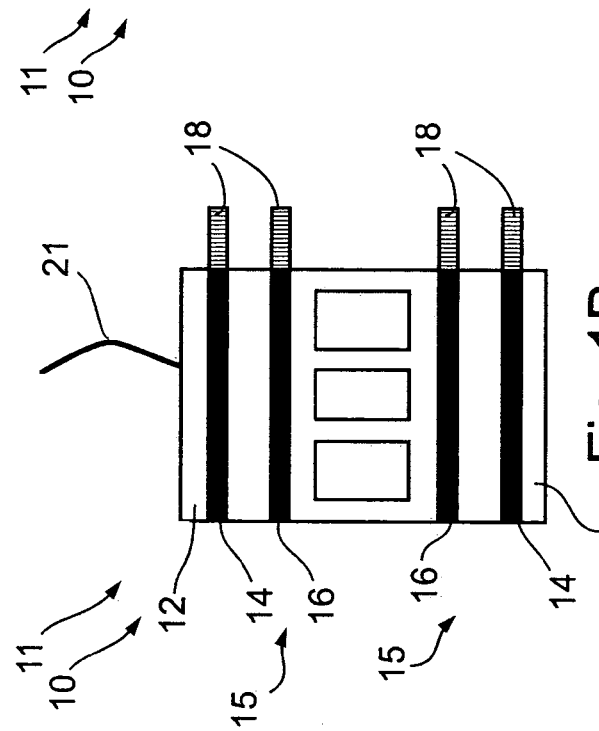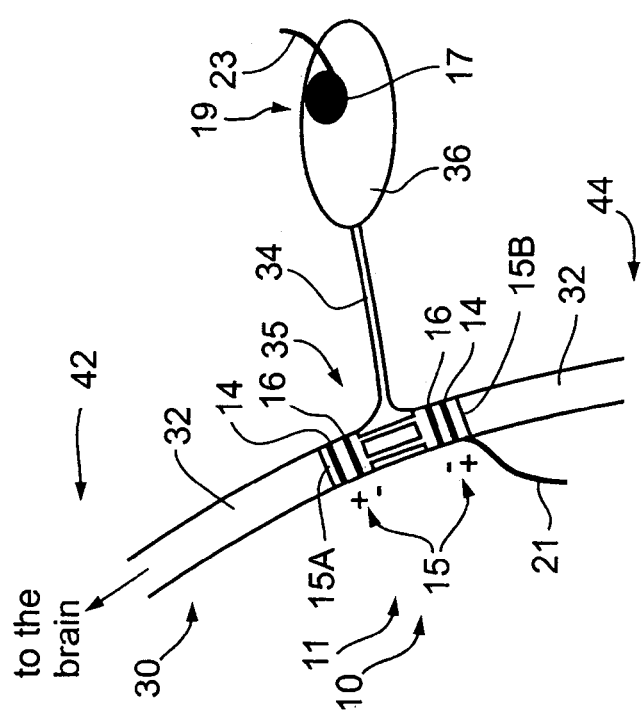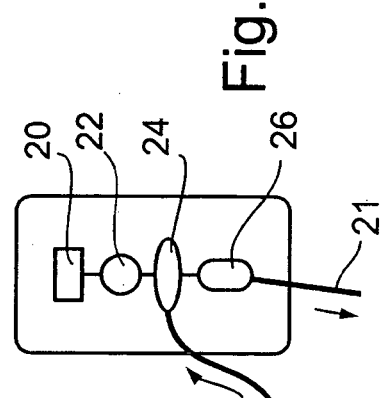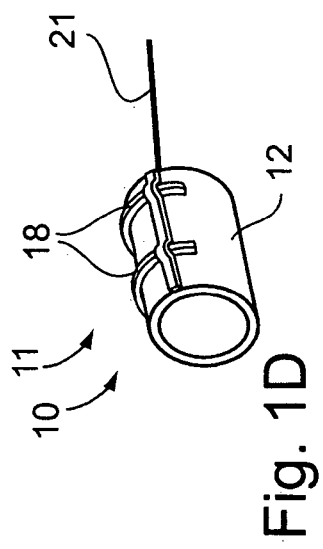

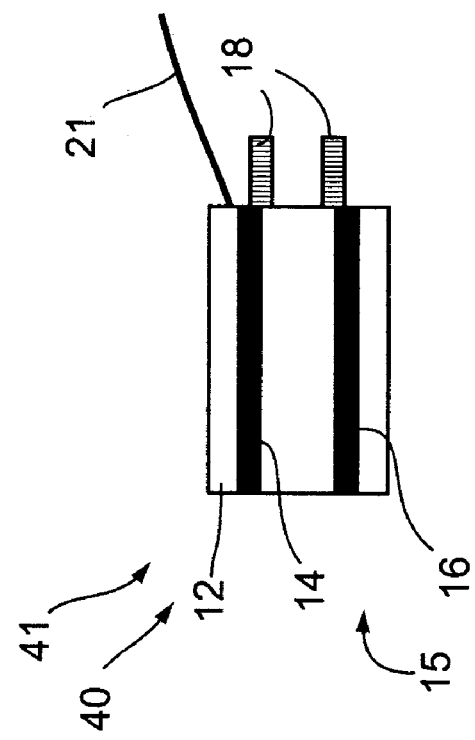
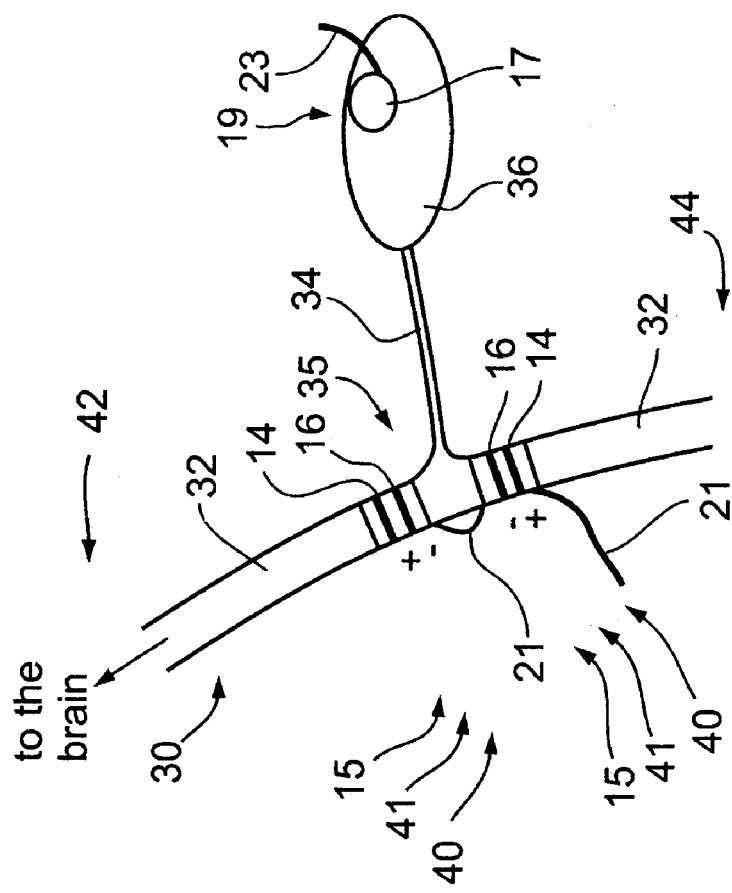

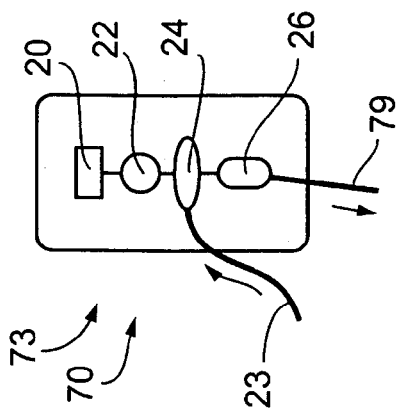
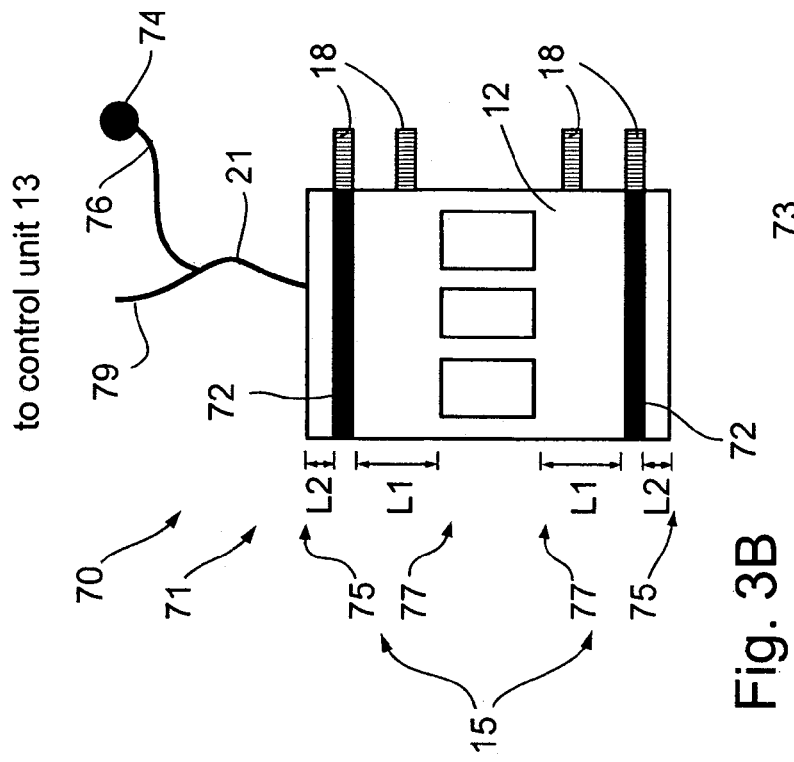
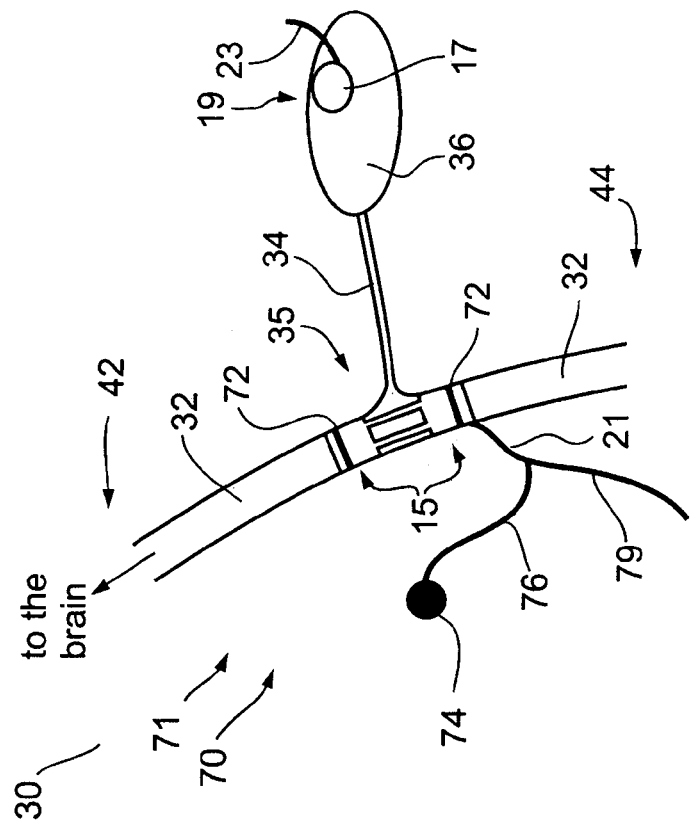
Fig. 3A
Fig. 3B
Fig. 3C

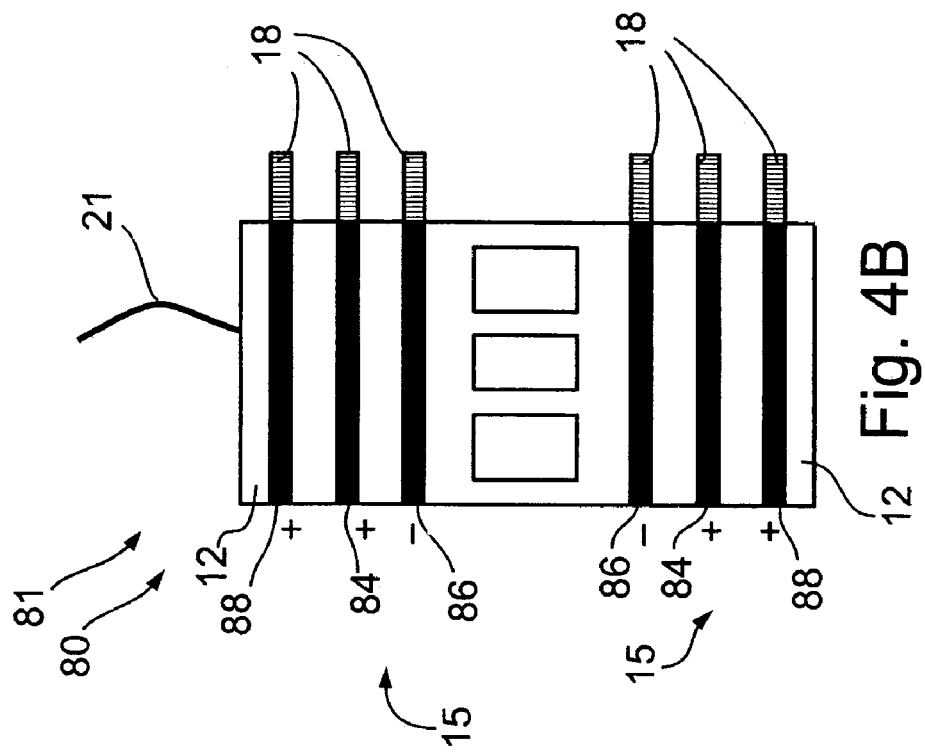
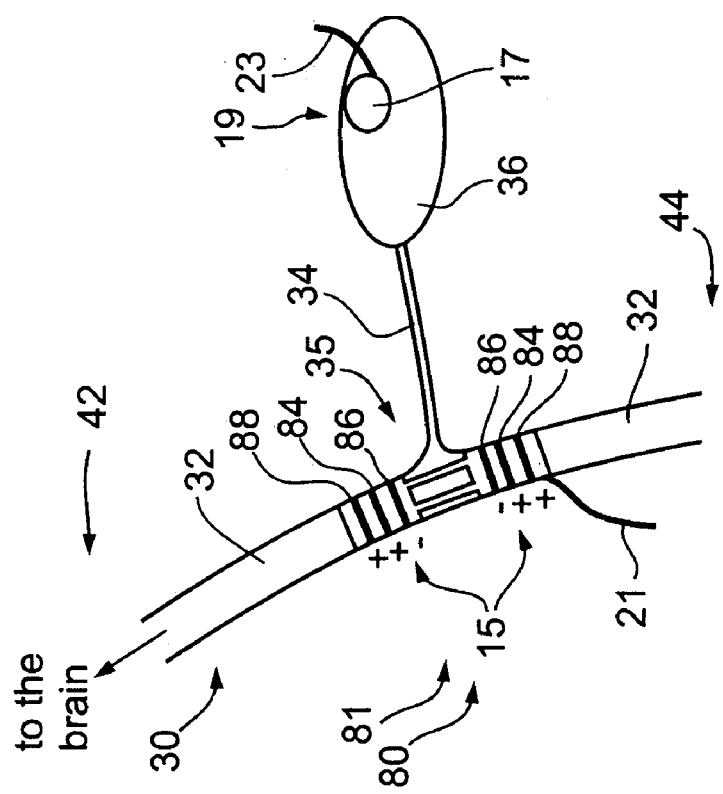
Fig. 4B
Fig. 4A

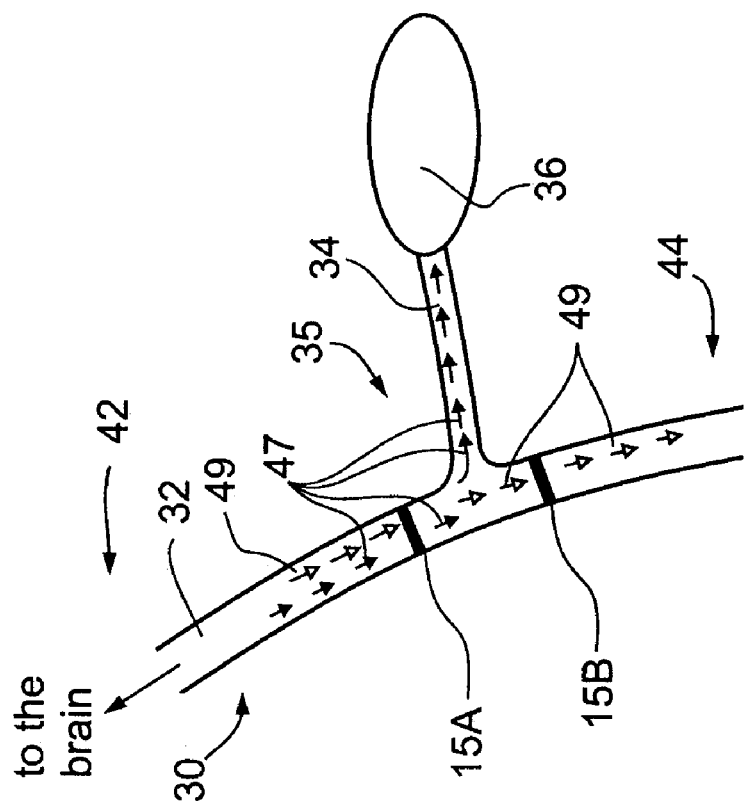
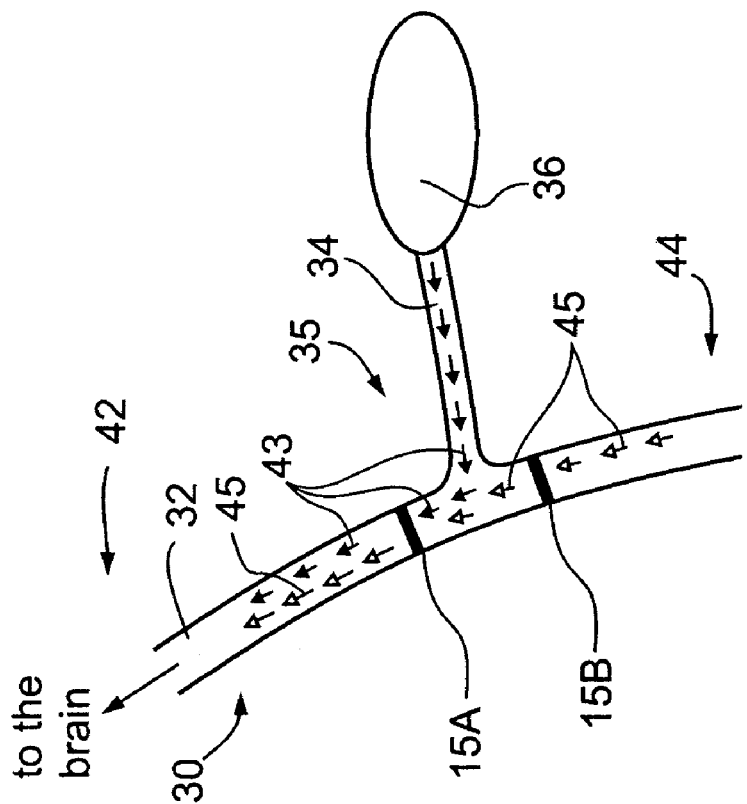

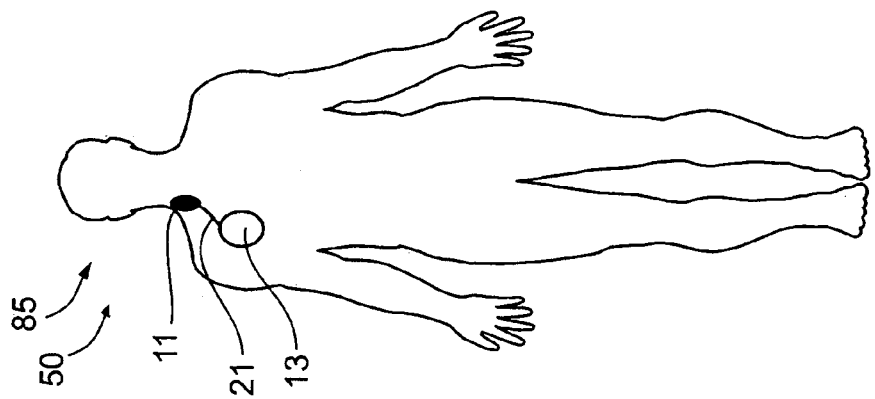
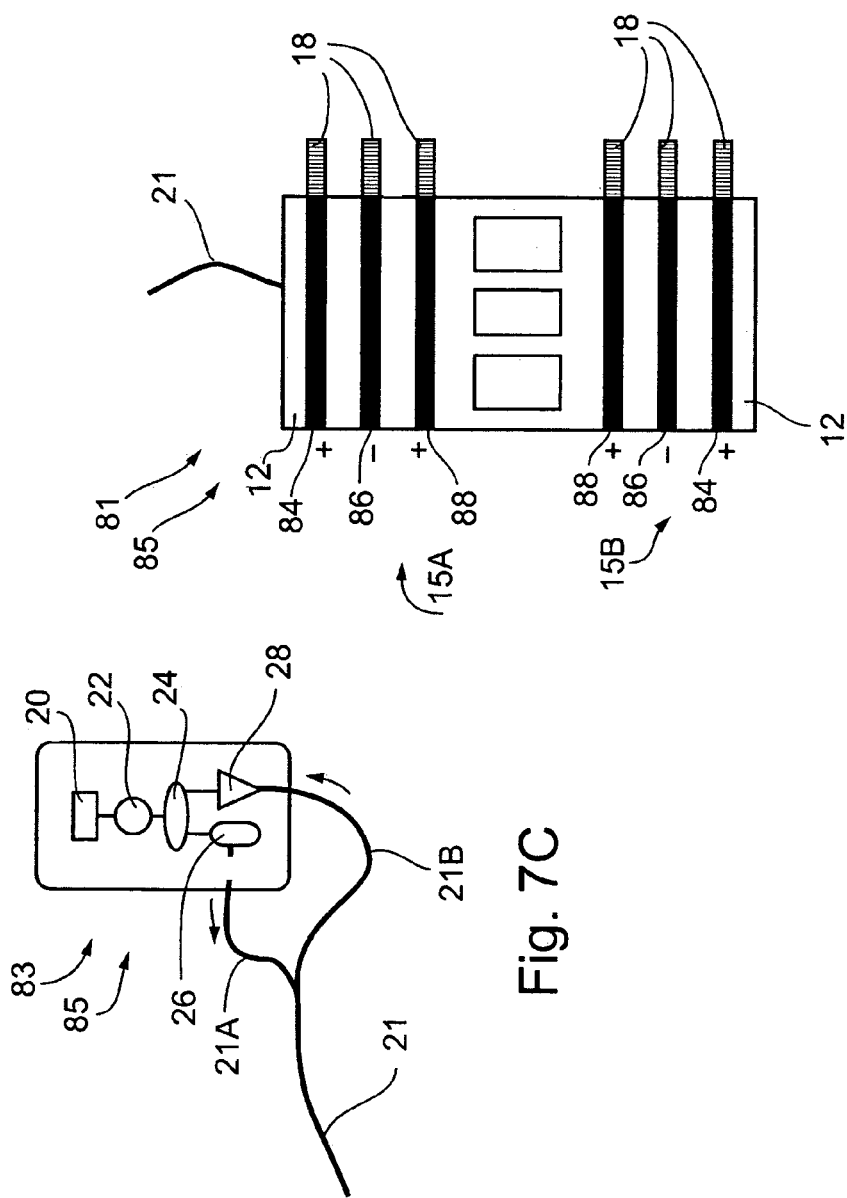

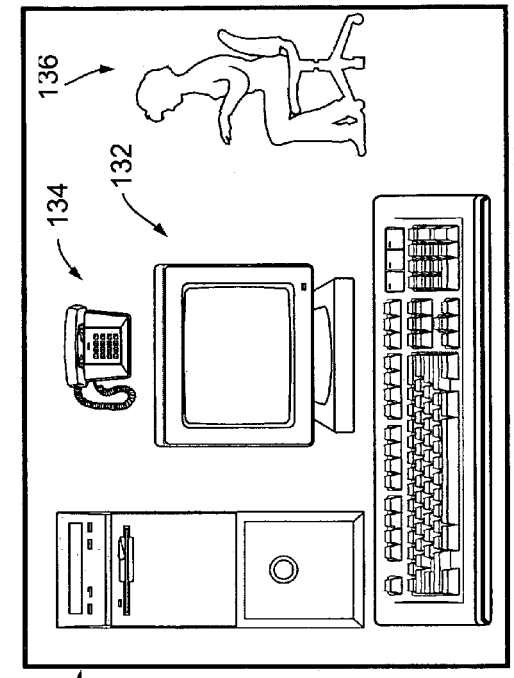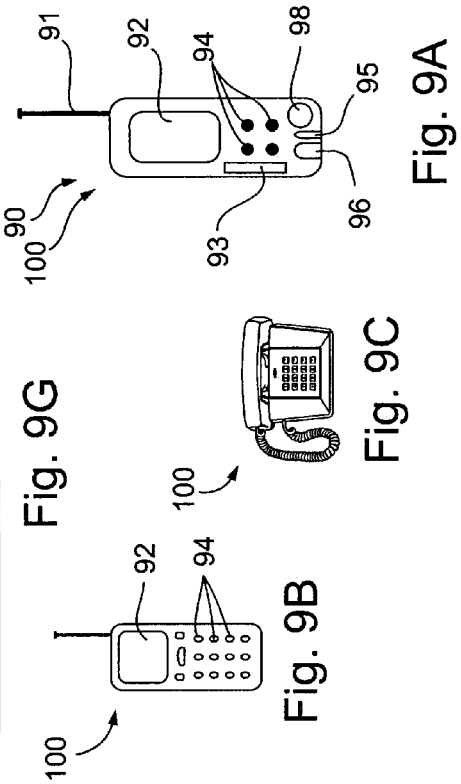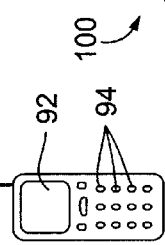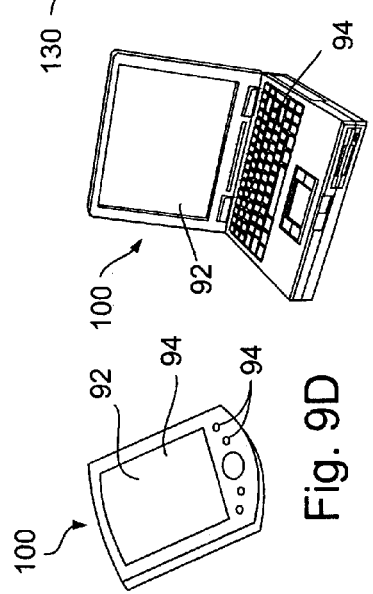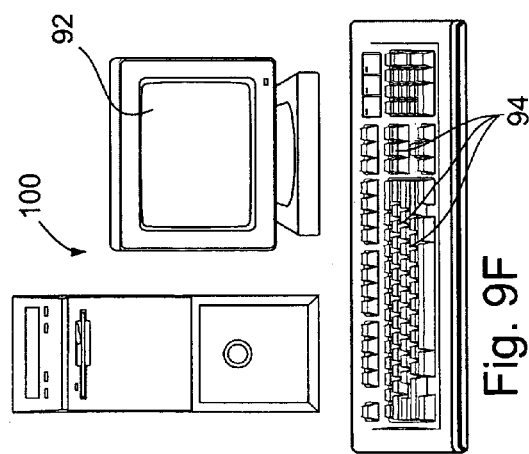

NERVE-BRANCH-SPECIFIC ACTION-POTENTIAL ACTIVATION, INHIBITION, AND MONITORING

FIELD AND BACKGROUND OF THE INVENTION

The present invention relates to nerve stimuli, and more particularly, to apparatus and methods for nerve-branch-specific action-potential activation, inhibition, and monitoring.

The nervous system is a network of billions of interconnected nerve cells, or neurons, that receive various types of stimuli and cause the body to respond appropriately. The neurons link the central nervous system (CNS) consisting of the brain and the spinal cord, with the body. A neuron usually has a cell body, dendrites that receive inputs, and an axon, an elongated nerve fiber that transmits electrical potentials as action potential. Efferent neurons send impulses peripherally to activate muscles or secretory cells, while afferent neurons convey sensory information centrally from the periphery.

The axon, the fiber-like, elongated portion of the nerve cell, conducts impulses in two directions, to and from the body of the nerve cell and transmits the information along the nervous system. Its function is somewhat analogous to a wire in an electric circuit. However, whereas in an electrical circuit, a wire allows the passage of a current, generally along its core, the axon, on the other hand, operates by the propagation of a potential difference along its plasma-membrane external surface, formed as a molecular lipid bilayer.

The propagating potential difference is referred to as action potential. It is an "all-or-nothing" phenomenon, described below:

1. Rest Condition: When at rest, sodium-potassium pumps in the plasma membrane keep a higher concentration of sodium ions outside the cell and a higher concentration of potassium ions inside, and create a voltage difference, of about 60-100 mV, generally referred to as the resting potential. Since the external surface is positive and the internal surface is negative, the membrane is polarized.

2. Depolarization: When the neuron is stimulated, a small region of the cell's membrane is depolarized to a threshold potential. When this happens, voltage-gated Na channels along the membrane open, and $Na^+$ ions rapidly diffuse into the cell, causing the electrical potential across the cell membrane to be reduced. As $Na^+$ ions continue to diffuse into the cell, an excess of positive ions accumulates inside, and the membrane becomes positively charged inside and negatively charged outside, at that small region. The action potential that is formed is typically about 20 mV. The voltage-gated Na channels then spontaneously close.

4. Propagation: The negatively charged membrane at the small region of the action potential stimulates the adjacent region to become depolarized. Thus the action potential propagates as a wave.

5. Repolarization: By the time the action potential has moved from one small region along the membrane to the adjacent region, the first region has repolarized and returned to its resting potential. Repolarization occurs as the $Na^+$ channels close and $K^+$ channels open, allowing $K^+$ ions to diffuse out of the cell more rapidly, restoring the positive charge to the external surface of the membrane, and the negative charge to the internal surface.

6. The Refractory Period: The refractory period is defined as the time period when an excitable membrane cannot be stimulated. It prevents the action potential from stimulating the region from which it came. In other words, it prevents reverberation between two adjacent regions. Thus, propagation must continue forward. During the refractory period, $Na^+$ ions are actively transported out of and $K^+$ into the cell by the Na—K pumps. The refractory period can be divided into two distinct portions:
   i. The absolute refractory period is the time during which no stimulus can initiate a new action potential.
   ii. The relative refractory period is the time during which a hyper-threshold stimulus can initiate an action potential.

The phase propagation process is very rapid, about 3 msec to a region, in myelinated fibers. Neurons typically fire at rates of 100 action potentials per second.

Because of the 'all-or-nothing characteristic of action potential, conduction is non-decremental, that is, it does not diminish, or 'die out' with distance from the initial site of stimulation. This is in marked contrast to conduction in a wire of an electrical circuit.

Neurons may be classified by conduction speed, diameter and the presence or absence of specialized lipoprotein insulation called myelin. The main nerve fibers, of about 2-20 microns in diameter, are myelinated, while the lower branches, down to about 0.2 microns in diameter, are unmyelinated. In myelinated fibers, conduction is saltatory, or by jumps, along the unmeylinated nodes of Ranvier. In unmyelinated nerve fibers, conduction is smooth.

Type A fibers are myelinated and can conduct impulses at 12-120 m/sec. Type B are also myelinated fibers but they only transmit impulses at 3-5 m/sec. Type C fibers are unmyelinated, small in diameter, and their conduction is very slow, at a rate of about 0.2-2.0 m/sec. An example of a Type A fiber is a motor efferent neuron innervating the gastrocnemius. An example of a Type B fiber is an autonomic preganglionic efferent neuron. An example of a Type C fiber is a sensory afferent neuron carrying information about diffused pain.

The refractory period of action-potential propagation makes nerve blocking possible. A number of blocking techniques are presently known for blocking or stimulating motor nerves controlling muscular or glandular activities. These include: (1) collision block; (2) high frequency block; and (3) anodal block.

In high frequency block, high frequency (e.g., 600 Hz) stimulations are used to block the transmission of the action potentials through the nerve fibers.

In anodal block, nerve fibers are locally hyperpolarized by a DC anodal current. If sufficiently hyperpolarized, action potentials are not able to propagate through the hyperpolarized zone and will be blocked. Anodal block is described, for example, in N. J. M. Rijkhof et al., "Acute Animal Studies on the Use of Anodal Block to Reduce Urethral Resistance in Sacral Root Stimulation" IEEE Transactions on Rehabilitation Engineering, Vol. 2, No. 2, pp. 92, 1994, whose disclosure is incorporated herein by reference.

In collision block, artificially induced action potentials are generated by a unidirectional electrode (an electrode adapted for generating an action-potential propagation substantially in one direction) and collide with, and thereby block, the naturally induced action potentials, coming towards them. In essence, the artificially induced action potential at a region along the axon membrane is timed and shaped so that when a naturally induced action potential arrives at that region, the region is in a refractory period, and the naturally induced action potential cannot propagate through it.

Collision block has been described, for example, in C. van den Honert, J. T. Mortimer "A Technique for Collision Blocks of Peripheral Nerve: Single Stimulus Analysis", IEEE Transactions on Biomedical Engineering, Vol. 28, No. 5, pp 373, 1981, whose disclosure is incorporated herein by reference.

The unidirectional electrode is an important component in collision blocking. Designs of unidirectional electrodes may be found, for example, in the following articles, Ungar I J et al., "Generation of unidirectionally propagating action potentials using a monopolar electrode cuff," Annals of Biomedical Engineering, 14:437-450 (1986), Sweeney J D et al., "An asymmetric two electrode cuff for generation of unidirectionally propagated action potentials," IEEE Transactions on Biomedical Engineering, vol. BME-33(6) (1986), and van den Honert C et al., "Generation of unidirectionally propagated action potentials in a peripheral nerve by brief stimuli," Science, 206(4424):1311-1312 (1979), whose disclosures are incorporated herein by reference.

Additionally, U.S. Pat. No. 4,649,936, to Ungar, et al., dated Mar. 17, 1987, and entitled, "Asymmetric single electrode cuff for generation of unidirectionally propagating action potentials for collision blocking," whose disclosure is incorporated herein by reference, describes a single electrode, having an asymmetric electrode cuff, which is disposed around a nerve trunk. A signal generator is connected between a cathode disposed asymmetrically in the electrode cuff and an anode disposed in an electrically conductive relationship within the body tissue. The signal generator applies a stimulus signal, which generates unidirectionally propagating action potentials on the nerve trunk. The electrode cuff includes a dielectric sleeve in which the cathode is positioned a first distance from an escape end and a second distance from an arrest end. The first distance is at least 1.7, and preferably about 7, times the second distance. This asymmetry causes a primary or forward stimulus signal current to be correspondingly greater than a secondary or reverse current.

Further work by the same group includes U.S. Pat. No. 4,628,942, to Sweeney, et al., dated, Dec. 16, 1986, and entitled, "Asymmetric shielded two electrode cuff," whose disclosure is incorporated herein by reference, and which describes an annular electrode cuff positioned around a nerve trunk, for imposing electrical signals on to the nerve trunk for the purpose of generating unidirectionally propagated action potentials. The electrode cuff includes an annular cathode having a circular passage therethrough of a first diameter. An annular anode has a larger circular passage therethrough of a second diameter, which second diameter is about 1.2 to 3.0 times the first diameter. A non-conductive sheath extends around the anode, cathode, and nerve trunk. The anode and cathode are placed asymmetrically to one side of the non-conductive sheath. Specifically, a first length along the electrode sheath between a first end and the cathode is at least twice a second length between the anode and cathode. A third length between the anode and a second end of the conductive sheath is smaller than the first or second lengths. With this geometry, the majority of the current applied to the anode electrode flows to the cathode along desired path segments with lesser amounts of current flowing in the less desired path segments.

Selective blocking relies on some combination of these techniques, for example, using a tripolar electrode formed as a cathode and primary and secondary anodes. In general, nerve stimulation is performed with the cathode. As the current is increased, fibers of lower diameters are "recruited," or stimulated. At a low current, only A fibers are activated, while at a higher current, both A and B fibers are activated. However, when it is desired to activate, for example, only B fibers, the current is divided between the primary and secondary anodes, such that while the cathode operates at a current that activate both A and B fibers, the primary anode inhibits A fibers, by hyper-polarization tuned specifically for these larger-diameter fibers. Thus an overall activation of B fibers is achieved, with the action potential propagation in the B fibers being towards the secondary anode. In this manner it is possible to predefine a range of nerve-fiber diameters and activate them specifically.

Techniques for selective blocking, have been described, for example, in D. M. Fitzpatrick et al., "A Nerve Cuff Design for the Selective Activation and Blocking of Myelinated Nerve Fibers", Ann. Conf. of the IEEE Eng. in Medicine and Biology Soc., Vol. 13, No. 2, pp. 906, 1991, describing a tripolar electrode device useful for this purpose. Also see N. J. M. Rijkhoff et al., "Orderly Recruitment of Motoneurons in an Acute Rabbit Model" Ann. Conf. of the IEEE Eng., Medicine and Biology Soc., Vol. 20, No. 5, pp. 2564, 1998; and R. Bratta et al., "Orderly Stimulation of Skeletal Muscle Motor Units with Tripolar Nerve Cuff Electrode", IEEE Transactions on Biomedical Engineering, Vol. 36, No. 8, pp. 836, 1989. The contents of the foregoing publications are incorporated herein by reference.

As taught by Fitzpatrick et al., the tripolar electrode used for muscle control includes a central cathode flanked on its opposite sides by two anodes. The central cathode generates action potentials in the motor nerve fiber by cathodic stimulation; one anode produces a complete anodal block in one direction so that the action potential produced by the cathode is unidirectional; and the other anode produces a selective anodal block to permit passage of the action potential in the opposite direction through selected motor nerve fibers to produce the desired muscle stimulation or suppression. Further details concerning the construction and operation of such tripolar electrodes are set forth in the above-cited publications incorporated herein by reference.

Additionally, J. F. X. Jones, Y. Wang, and D. Jordan (1995): Heart Rate Response to Selective Stimulation of Cardiac Vagal C-Fibers in Anesthetized Cats, Rats, and Rabbits," J. Physiol., 489, 203-214, incorporated herein by reference, describes the use of two bipolar electrodes to stimulate only a certain group of fibers (for example, only C-fibers), based on their diameters.

Additionally, commonly owned U.S. Pat. No. 6,600,954 to Cohen et al., dated Jul. 29, 2003, and entitled, "Method and Apparatus for Selective Control of Nerve Fibers," whose disclosure is incorporated herein by reference, describes a method and apparatus particularly useful for pain control by selectively blocking the propagation of body-generated action potentials traveling through a nerve bundle by using a tripolar electrode device to generate unidirectional action potentials to serve as collision blocks with the body-generated action potentials representing pain sensations in the small-diameter sensory fibers. In the described preferred embodiments there are a plurality of electrode devices spaced along the length of the nerve bundle which are sequentially actuated with delays corresponding to the velocity of propagation of the body-generated action potentials through the large-diameter fibers to produce a "green wave" effect which minimizes undesired anodal blocking of the large-diameter fibers while maximizing the collision blocking of the small-diameter fibers.

Furthermore, commonly owned US Patent Application US20030045914, to Cohen et a., published on Mar. 6, 2003 and entitled, "Treatment of Disorders by Unidirectional Nerve Stimulation," whose disclosure is incorporated herein by reference, describes an apparatus for treating a condition of a subject. An electrode device is adapted to be coupled to longitudinal nervous tissue of the subject, and a control unit is adapted to drive the electrode device to apply to the nervous tissue a current, which is capable of inducing action potentials that propagate in the nervous tissue in a first direction, so as to treat the condition. The control unit is further adapted to suppress action potentials from propagating in the nervous tissue in a second direction opposite to the first direction.

A problem with nerve activation is a "virtual cathode effect," or a "virtual anode effect," which causes some interference, as follows:

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j$$

where U is the potential, σ is the conductance tensor specifying the conductance of the various materials (electrode housing, axon, intracellular fluid, etc.), and j is a scalar function representing the current source density specifying the locations of current injection. The activation function is found by solving this partial differential equation for U. If the axon is defined to lie in the z direction, then the activation function is:

$$AF = \frac{\partial^2 U}{\partial z^2}$$

In a simple, illustrative example of a point electrode located a distance d from the axis of an axon in a uniformly-conducting medium with conductance σ, the two equations above are solvable analytically, to yield:

$$AF = \frac{I_{el}}{4\pi\rho} \frac{2z^2 - d^2}{(z^2 + d^2)^{2.5}}$$

where $I_{el}$ is the electrode current. It is seen that when σ and d are held constant, and for a constant positive $I_{el}$ (to correspond to anodal current), the minimum value of the activation function is negative, and is attained at z=0, i.e., at the point on the nerve closest to the source of the anodal current. Thus, the most negative point on the activation function corresponds to the place on a nerve where hyperpolarization is maximized, namely at the point on the nerve closest to the anode.

Additionally, this equation predicts positive "lobes" for the activation function on either side of z=0, these positive lobes peaking in their values at a distance which is dependent on each of the other parameters in the equation. The positive values of the activation function correspond to areas of depolarization, a phenomenon typically associated with cathodic current, not anodal current. However, it has been shown that excess anodal current does indeed cause the generation of action potentials adjacent to the point on a nerve corresponding to z=0, and this phenomenon is therefore called the "virtual cathode effect." (An analogous, but reverse phenomenon, the "virtual anode effect" exists responsive to excess cathodic stimulation.)

US Patent Application 20030050677, to Gross, et al., entitled, "Electrode assembly for nerve control," whose disclosure is incorporated herein by reference, describes an apparatus for applying current to a nerve, the apparatus being designed also to reduce the virtual cathode effect. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site. For most applications, the secondary anodal current is of lower magnitude than the primary anodal current. In this manner, the "virtual cathode" effect induced by the primary anodal current is minimized. As described hereinabove, the virtual cathode effect can stimulate, rather than block, the generation of action potentials in fibers in a region adjacent to the application of anodal current of a sufficiently high magnitude. In accordance with the teaching of US Patent Application 20030050677, to Gross, et al., application of the primary and secondary anodal currents in appropriate ratios is configured to generally minimize the virtual cathode effect. Typically, but not necessarily, the ratio of the primary to the secondary anodal current ranges from 5:1 to 10:1. Additionally, the apparatus of US Patent Application 20030050677 may include a housing to which the cathode and a plurality of anodes are coupled, wherein one of the anodes is positioned within the housing so as to reduce a virtual cathode effect induced by another one of the anodes.

The Vagus nerve (the tenth cranial nerve) has been the subject of considerable research in nerve stimulation. It is composed of somatic and visceral afferents and efferents, and is responsible for controlling and (or) receiving feedback from various glands, the pharynx, larynx, heart, lungs, liver, stomach, intestine, and uterus. Because of its large number of functions with respect to a range of body systems, the Vagus nerve is preferred in many applications for purposes of modulating the functions of designated organs or portions of the central nervous system.

Nerve blocking along a major nerve trunk such as the Vagus nerve may be achieved by implanting an electrode along the trunk, which is large enough, and visible. Yet, such blocking affects the large plurality of nerve branches that emerge from the trunk, and their respective organs, without discrimination. However, in general, discrimination is important, and it is generally desired to target only a specific organ. Because the nerve fibers leading to the specific organs are very fine, implanting an electrode along it is technically difficult. There is thus a need for activating, inhibiting, and

SUMMARY OF THE INVENTION

In accordance with one aspect of the present invention, there is thus provided a dual electrode arrangement, for nerve-branch-specific, action-potential association, comprising:

a proximal electrode configuration, implanted on a nerve trunk, proximally to a junction of the nerve trunk with a preselected nerve branch; and a distal electrode configuration, implanted on the nerve trunk, distally to the junction.

In accordance with an additional aspect of the present invention, the proximal electrode configuration is a cathode, adapted to generate an action-potential propagation, and the distal electrode configuration is an anode, adapted to block an action potential propagation, by hyperpolarization.

In accordance with an additional aspect of the present invention, the electrode configurations include spacers for preventing direct contact between a metal and a nerve tissue.

In accordance with an additional aspect of the present invention, the proximal and distal electrode configurations are unidirectional electrode configurations, each adapted for generating an action-potential propagation substantially in one direction, the unidirectional electrode configurations being arranged as mirror images to each other, so that the generated action-potential propagations are towards each other.

In accordance with an additional aspect of the present invention, the unidirectional electrode configurations are monopolar, unidirectional electrode configurations.

In accordance with an alternative aspect of the present invention, the unidirectional electrode configurations are bipolar, unidirectional electrode configurations.

In accordance with an alternative aspect of the present invention, the unidirectional electrode configurations are tripolar, unidirectional electrode configurations.

In accordance with an alternative aspect of the present invention, the unidirectional electrode configurations are multipart, unidirectional electrode configurations.

In accordance with an additional aspect of the present invention, the nerve-branch-specific, action-potential association is selected from the group consisting of:

generating efferent action-potential propagations, substantially restricted to the preselected nerve branch;

inhibiting afferent action-potential propagations, from the preselected nerve branch;

selectively generating action-potential propagations, in a subset of nerve fibers of a predetermined diameter range, substantially restricted to the preselected nerve branch;

selectively inhibiting action-potential propagations, in a subset of nerve fibers of a predetermined diameter range, substantially restricted to the preselected nerve branch;

monitoring naturally-occurring, efferent action-potential propagations, heading towards the preselected nerve branch; and monitoring naturally-occurring, afferent action-potential propagations, from the preselected nerve branch.

In accordance with another aspect of the present invention, there is thus provided an apparatus, for nerve-branch-specific, action-potential association, comprising:

a dual electrode arrangement, which comprises:

a proximal electrode configuration, implanted on a nerve trunk, proximally to a junction of the nerve trunk with a preselected nerve branch; and a distal electrode configuration, implanted on the nerve trunk, distally to the junction; and an electronic unit, in signal communication with the dual electrode arrangement.

In accordance with an additional aspect of the present invention, the electronic unit comprises a controller.

In accordance with an additional aspect of the present invention, the electronic unit comprises a sensor unit, in communication with the controller.

In accordance with an additional aspect of the present invention, the electronic unit comprises a pulse generator.

In accordance with an additional aspect of the present invention, the electronic unit comprises an amplification component.

In accordance with an additional aspect of the present invention, the electronic unit comprises a receiver.

In accordance with an additional aspect of the present invention, the electronic unit comprises a transmitter.

In accordance with an additional aspect of the present invention, the unidirectional electrode configurations are activated by a stimulation current which is no greater than 20 mA.

In accordance with another aspect of the present invention, there is thus provided a method for nerve-branch-specific, action-potential association, comprising:

implanting a proximal electrode configuration, on a nerve trunk, proximally to a junction of the nerve trunk with a preselected nerve branch;

implanting a distal electrode configuration, on the nerve trunk, distally to the junction; and providing an electronic unit, in signal communication with the proximal and distal electrode configurations.

In accordance with an additional aspect of the present invention, the proximal and distal electrode configurations are unidirectional electrode configurations, arranged as mirror images to each other, so that the generated action-potential propagations are towards each other.

In accordance with an additional aspect of the present invention, the method comprises generating efferent action-potential propagations, substantially restricted to the preselected nerve branch.

In accordance with an additional aspect of the present invention, the method comprises inhibiting afferent action-potential propagations, from the preselected nerve branch.

In accordance with an additional aspect of the present invention, the method comprises selectively generating action-potential propagations, in a subset of nerve fibers of a predetermined diameter range, substantially restricted to the preselected nerve branch.

In accordance with an additional aspect of the present invention, the method comprises selectively inhibiting action-potential propagations, in a subset of nerve fibers of a predetermined diameter range, substantially restricted to the preselected nerve branch.

In accordance with an additional aspect of the present invention, the method comprises monitoring naturally-occurring, efferent action-potential propagations, heading towards the preselected nerve branch.

In accordance with an additional aspect of the present invention, the method comprises monitoring naturally-occurring, afferent action-potential propagations, from the preselected nerve branch.

In accordance with an additional aspect of the present invention, the method comprises activating the electrode configurations in accordance with a predetermined schedule.

In accordance with an additional aspect of the present invention, the method comprises activating the electrode configurations simultaneously.

In accordance with another aspect of the present invention, there is thus provided a set of unidirectional electrodes, located around a nerve branch, configured to generate action-potential propagations only in the nerve branch.

In accordance with an additional aspect of the present invention, the set of unidirectional electrodes is configured to generate action-potential propagations in the nerve branch, to affect an organ.

In accordance with an additional aspect of the present invention, the set of unidirectional electrodes is configured to block afferent action potential originating from an organ.

In accordance with an additional aspect of the present invention, the set of unidirectional electrodes is configured to selective activate and block action potential associated with the nerve branch, by stimulating only a sub set of nerve fibers, selected according to their fiber velocity.

In accordance with an additional aspect of the present invention, the set of unidirectional electrodes is monopolar.

In accordance with an additional aspect of the present invention, the set of unidirectional electrodes is bipolar.

In accordance with an additional aspect of the present invention, the set of unidirectional electrodes is tripolar.

In accordance with an additional aspect of the present invention, the set of unidirectional electrodes is configured to be activated simultaneously.

In accordance with an additional aspect of the present invention, the set of unidirectional electrodes is configured to be activated by a stimulation current which is no greater than 20 mA.

The present invention successfully addresses the shortcomings of the presently known configurations by providing a dual electrode arrangement, wherein two, preferably unidirectional, electrode configurations flank a nerve junction from which a preselected nerve branch issues, proximally and distally to the junction, with respect to the brain. The arrangement is conducive to the following: generating efferent action-potential propagations, substantially restricted to the preselected nerve branch, inhibiting afferent action-potential propagations, from the preselected nerve branch, selectively generating action-potential propagations, in a subset of nerve fibers of a predetermined diameter range, substantially restricted to the preselected nerve branch, and selectively inhibiting action-potential propagations, in a subset of nerve fibers of a predetermined diameter range, substantially restricted to the preselected nerve branch. The dual electrode arrangement is further conducive to monitoring naturally-occurring, efferent action-potential propagations, heading towards the preselected nerve branch, and monitoring naturally-occurring, afferent action-potential propagations, from the preselected nerve branch. The unidirectional electrode configurations may be monopolar, bipolar, tripolar, or multipolar. Communication with extracorporeal stations, and closed loop operations are also provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1J schematically illustrate an intracorporeal apparatus for activating or inhibiting action-potential propagations, in a preselected nerve branch, in accordance with a preferred embodiment of the present invention;

FIGS. 2A and 2B schematically illustrate an intracorporeal apparatus for activating or inhibiting action-potential propagations, in a preselected nerve branch, in accordance with another preferred embodiment of the present invention;

FIGS. 3A-3C schematically illustrate an intracorporeal apparatus for activating or inhibiting action-potential propagations, in a preselected nerve branch, in accordance with still another preferred embodiment of the present invention;

FIGS. 4A and 4B schematically illustrate an intracorporeal apparatus, in accordance with another preferred embodiment of the present invention;

FIGS. 7A-7F schematically illustrate an intracorporeal apparatus for monitoring, activating, inhibiting, selectively activating, or selectively inhibiting action-potential propagations, in a preselected nerve branch, in accordance with yet another preferred embodiment of the present invention;

FIGS. 9A-9G schematically illustrate extracorporeal systems, in accordance with the present invention;

DESCRIPTION OF THE PREFERRED EMBODIMENTS

Figure 1G:
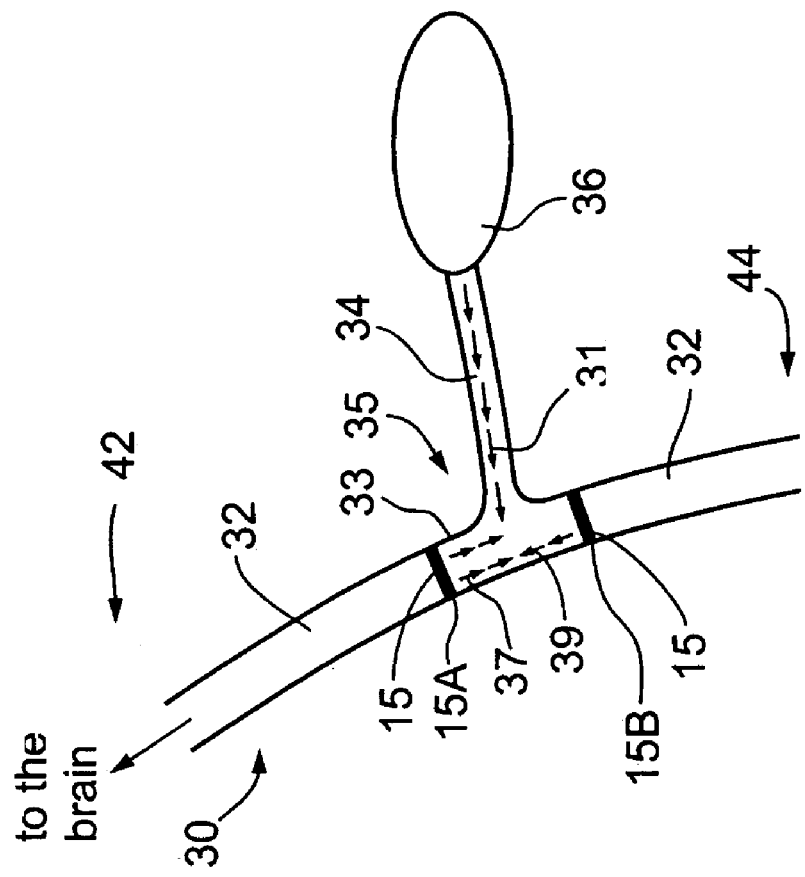

The present invention is of a dual electrode arrangement, wherein two, preferably unidirectional, electrode configurations flank a nerve junction from which a preselected nerve branch issues, proximally and distally to the junction, with respect to the brain. Specifically, the arrangement is conducive to the following: generating efferent action-potential propagations, substantially restricted to the preselected nerve branch, inhibiting afferent action-potential propagations, from the preselected nerve branch, selectively generating action-potential propagations, in a subset of nerve fibers of a predetermined diameter range, substantially restricted to the preselected nerve branch, and selectively inhibiting action-potential propagations, in a subset of nerve fibers of a predetermined diameter range, substantially restricted to the preselected nerve branch. The dual electrode arrangement is further conducive to monitoring naturally-occurring, efferent action-potential propagations, heading towards the preselected nerve branch, and monitoring naturally-occurring, afferent action-potential propagations, from the preselected nerve branch. The unidirectional electrode configurations may be monopolar, bipolar, tripolar, or multipolar. Communication with extracorporeal stations, and closed loop operations are provided.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Referring now to the drawings, FIGS. 1A-1J schematically illustrate an intracorporeal apparatus 10 for activating or inhibiting action-potential propagations, in a preselected nerve branch, in accordance with a preferred embodiment of the present invention.

Apparatus 10 includes a cuff 11 (FIGS. 1A-1D), which houses electrode configurations 15, a control unit 13 (FIG. 1E), and preferably also, a sensor unit 19 (FIGS. 1A and 1H), which is preferably intracorporeal.

As seen in FIGS. 1A and 1B, cuff 11 includes two unidirectional-electrode configurations 15, a proximal configuration 15A and a distal configuration 15B. Each is adapted for generating an action-potential propagation substantially in one direction, the unidirectional electrode configurations being arranged as mirror images to each other, so that the generated action-potential propagations are towards each other.

Unidirectional-electrode configurations 15 are positioned at a junction 35 of a nerve structure 30, so as to flank a preselected nerve branch 34, issuing from a trunk 32 and leading to an organ 36. Junction 35 defines a proximal side 42 and a distal side 44, with respect to the brain, and cuff 11 is positioned with two unidirectional-electrode configurations 15 being proximally and distally to junction 35.

In accordance with the present embodiment, unidirectional-electrode configurations 15 are bipolar, each formed as two conductive strips of an anode 14 and a cathode 16, for example, of stainless steel, titanium, tantalum, gold, platinum, iridium, or another biocompatible, conductive substance. A cable 21 provides communication with control unit 13.

It will be appreciated that other unidirectional-electrode arrangements are similarly possible, for example, as described hereinbelow, in conjunction with FIGS. 2A-6

As seen in a side view of cuff 11, in FIG. 1C, cuff 11 is constructed to form an insulating sleeve 12, for example, of silicon, natural rubber, plastic, or the like, which houses electrode configurations 15. Preferably, electrodes 14 and 16 are not flush with a proximal surface 25 with respect to the tissue. Rather, spacers 9 are provided to prevent the metal surface of electrodes 14 and 16 from making direct contact with the nerve tissue. Preferably spacers 9 are formed of the same material as insulating sleeve 12, or of a similar material, as taught in US Patent Application 20030050677, to Gross, et al., entitled, "Electrode assembly for nerve control," whose disclosure is incorporated herein by reference. Additionally, spacers 9 provide for insulating electrodes 14 and 16 from each other.

As seen in FIG. 1D, sleeve 12 is preferably designed to close over nerve trunk 32, preferably, with a locking mechanism 18, preferably adjusting to the diameter of nerve trunk 32. When sleeve 12 is closed, unidirectional-electrode configurations 15 may be designed to form rings around nerve trunk 32.

In accordance with the present invention, cuff 11 is designed for implantation around a nerve trunk, for example, the Vagus nerve trunk or the Pudental nerve trunk, at a nerve-branch junction, for example, in the neck region, for the Vagus nerve. Examples of nerve-trunk junctions, in accordance with the present invention, are illustrated hereinbelow, in conjunction with FIGS. 12A and 12B.

As seen in FIG. 1E, control unit 13 of apparatus 10 includes a power source 20, for supplying power to apparatus 10, a receiver 22, or a transceiver 22 for receiving instructions from an extracorporeal station, described hereinbelow, in conjunction with FIGS. 9A-9G, and a controller 24, which may be a dedicated circuit, a processor, an Application Specific Integrated Circuit (ASIC), or a microcomputer, as known. Controller 24 activates a pulse generator 26, which drives electrode configurations 15, via cable 21.

In accordance with the present invention, control unit 13 is designed for implantation percutaneously, preferably in the chest area. Tunneling under the skin may be used to implant cable 21, connecting control unit 13 in the chest area and cuff 11 in the neck region.

Figure 1F:
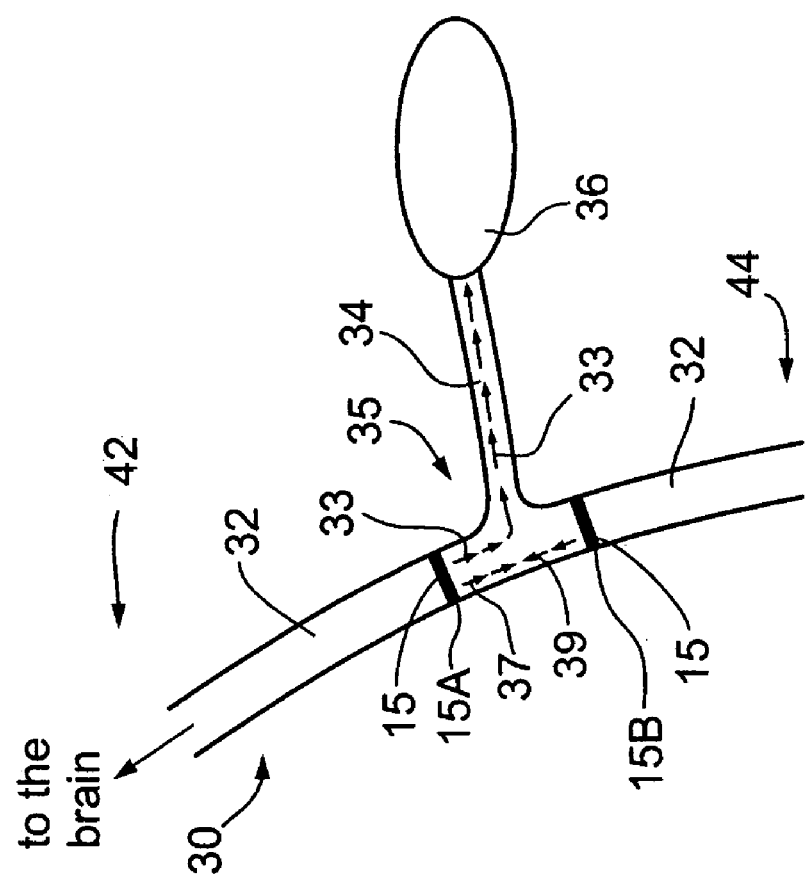

The operation of apparatus 10 is best understood with reference to FIGS. 1F and 1G.

FIG. 1F illustrates a situation of nerve-branch-specific activation. Preferably, two electrode configurations 15A and 15B are activated simultaneously, generating action potentials 37 and 39, which propagate towards each other, so as to generate refractory periods for each other, when they meet. In this manner, substantial collision blocking of action potentials 37 and 39 occurs.

However, since the nerve fibers from the brain to preselected nerve branch 34 and to organ 36 do not communicate with distal electrode configuration 15B, an action potential 33, generated by proximal electrode configuration 15A, in these nerve fibers, has no corresponding action potential generated by distal electrode configuration 15B. Action potential 33 will thus travel to organ 36, uninterrupted. In this manner, substantial nerve-branch specific activation takes place, allowing artificially induced action potentials to propagate substantially only through preselected nerve branch 34.

The action potentials are thus substantially confined to the nerve region enclosed by electrode configurations 15.

The stimulation current is preferably no greater than 20 mA, but it will be appreciated that this value may be exceeded.

FIG. 1G illustrates a situation of nerve-branch-specific inhibition, of an afferent action potential 31, which originates from organ 36. Again, two electrode configurations 15 are activated simultaneously, generating action potentials 37 and 39, which propagate towards each other, so as to generate refractory periods for each other, when they meet. Additionally, action potential 33, generated by proximal electrode configuration 15A, in the nerve fibers leading to organ 36 will generate a refractory period for an action potential 31 from organ 36, when they meet, thus substantially inhibiting action potential 31 from organ 36. In this manner, substantial nerve-branch inhibition takes place, specific to preselected nerve branch 34.

The action potentials are again substantially confined to the nerve region enclosed by electrode configurations 15.

It will be appreciated that nerve branch 34 may be very fine, and implanting an electrode directly on it may be technically difficult. However, implanting cuff 11 on nerve trunk 32 is feasible. In accordance with the present invention, action potential may be induced to propagate only along nerve branch 34, even as cuff 11 is mounted on larger trunk 32.

Figure 1J:
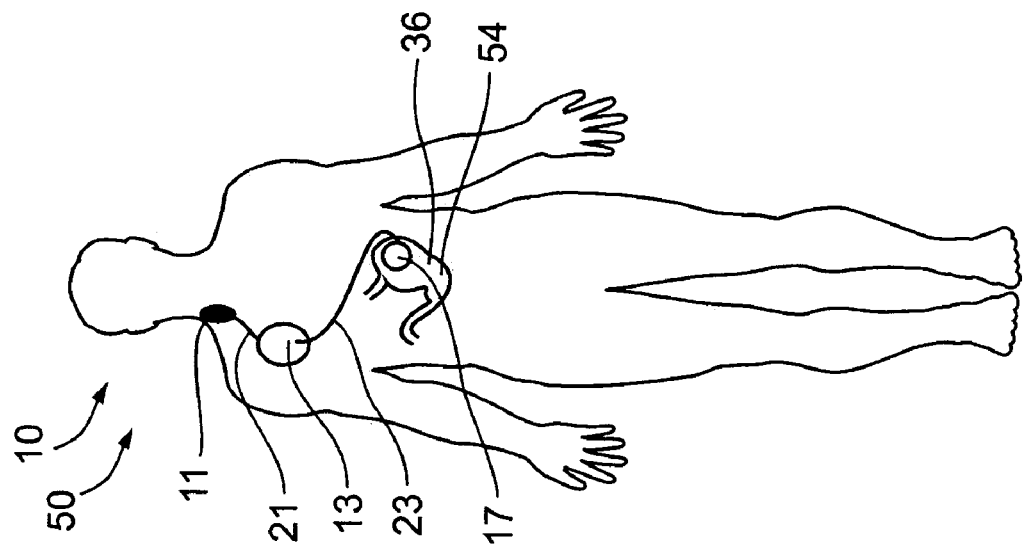
Figure 1I:
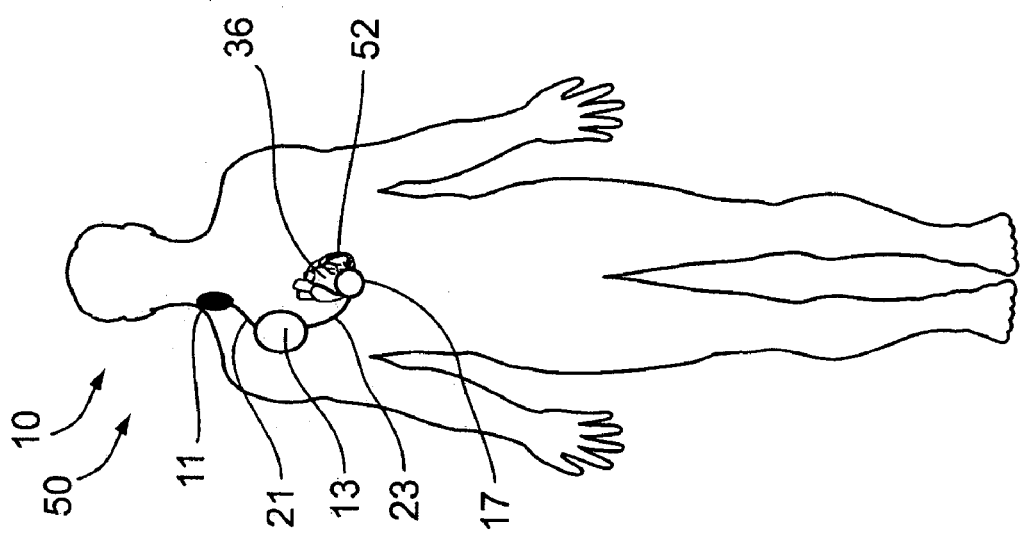
Figure 1H:
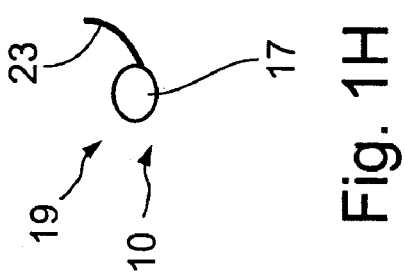

As seen in FIGS. 1A and 1H, apparatus 10 may further include intracorporeal sensor unit 19, which includes a physiological sensor 17, for sensing a physiological condition associated with organ 36. A cable 23 connects sensor 17 to controller 24 of control unit 13. It will be appreciated that an amplifying component may also be used, either incorporated to sensor unit 19, or to control unit 13, or to both.

Organ 36 may be a heart, and sensor 17 may be, for example, a heart-rate sensor, for detecting periods of sleep, or an electrocardiograph (EKG) sensor for detecting an onset of seizure. Alternatively, organ 36 may be a stomach, and sensor 17 may be, for example, an acid sensor, for sensing stomach acid, or a tensile sensor, for sensing muscle contractions. Alternatively a pressure sensor may be used, for sensing the blood flow rate. It will be appreciated that other physiological sensors, may be used, and may be adapted for other organs.

Sensor unit 19 is designed for implantation within organ 36 (FIG. 1A), while communicating with control unit 13 via a cable 23. Again, tunneling may be used to pass cable 17, connecting control unit 13 in the chest area and sensor unit 19, in organ 36. It will be appreciated that wireless communication between sensor unit 19 and control unit 13 is also possible, for example, by ultrasound, IR, or RF.

FIG. 1I illustrates apparatus 10, which is implanted in a person 50, wherein cuff 11 is implanted in the neck region, control unit 13 is implanted in the chest area, and sensor unit 19 is implanted in a heart 52, heart 52 being organ 36 in this case.

Alternatively, FIG. 1J illustrates apparatus 10, which is implanted in person 50, wherein sensor unit 19 is implanted in a stomach 54, stomach 54 being organ 36 in that case.

In accordance with another preferred embodiment of the present invention, bipolar unidirectional electrode configurations 15 may be designed according to the teaching of U.S. Pat. No. 4,628,942, to Sweeney, et al., entitled, "Asymmetric shielded two electrode cuff," whose disclosure is incorporated herein by reference. Sweeney, et al. teach an annular electrode cuff positioned around a nerve trunk, for imposing electrical signals on to the nerve trunk for the purpose of generating unidirectionally propagated action potentials. The electrode cuff includes an annular cathode having a circular passage therethrough of a first diameter. An annular anode has a larger circular passage therethrough of a second diameter, which second diameter is about 1.2 to 3.0 times the first diameter. A non-conductive sheath extends around the anode, cathode, and nerve trunk. The anode and cathode are placed asymmetrically to one side of the non-conductive sheath. Specifically, a first length along the electrode sheath between a first end and the cathode is at least twice a second length between the anode and cathode. A third length between the anode and a second end of the conductive sheath is smaller than the first or second lengths. With this geometry, the majority of the current applied to the anode electrode flows to the cathode along desired path segments with lesser amounts of current flowing in the less desired path segments.

When using two unidirectional electrode configurations 15, wherein each is designed according to the teaching of U.S. Pat. No. 4,628,942, to Sweeney, et al., the mirror image arrangement is preferably, cathode to cathode, as taught in conjunction with FIGS. 1A-1C. Two unidirectional electrode configurations 15 may be arranged on a single cuff, for example, as shown in conjunction with FIGS. 1A-1C, or on two separate cuffs, as shown in conjunction with FIGS. 2A-2B.

It will be appreciated that other bipolar unidirectional electrode configurations are possible and are within the scope of the present invention.

Referring further to the drawings, FIGS. 2A and 2B schematically illustrate an intracorporeal apparatus 40 for activating or inhibiting action-potential propagations, in preselected nerve branch 34, in accordance with another preferred embodiment of the present invention.

Apparatus 40 includes two cuffs 41, each comprising a single unidirectional electrode configuration 15, wherein cuffs 41 are arranged as mirror images to each other and are connected with cable 21. In other respects, apparatus 40 of the present embodiment is similar to apparatus 10 of FIGS. 1A-1J.

Referring further to the drawings, FIGS. 3A-3C schematically illustrate an intracorporeal apparatus 70 for activating or inhibiting action-potential propagations, in preselected nerve branch 34, in accordance with still another preferred embodiment of the present invention.

Apparatus 70 includes an asymmetrical cuff 71, comprising two monopolar, unidirectional electrode configurations 15, arranged as mirror images to each other, so that the generated action-potential propagations are towards each other.

Preferably, each monopolar unidirectional electrode configuration 15 is designed in accordance with the teachings of U.S. Pat. No. 4,649,936, to Ungar, et al., entitled, "Asymmetric single electrode cuff for generation of unidirectionally propagating action potentials for blocking," whose disclosure is incorporated herein by reference. Ungar, et al. teach a unidirectional electrode configuration of a single electrode, positioned in an asymmetric electrode cuff, formed of a dielectric sleeve. A cathode 72 is positioned at a first distance L1 from an escape end 77 and at a second distance L2 from an arrest end 75. First distance L1 is at least 1.7, and preferably about 7 times second distance L1.

An anode 74 is physically disconnected from cuff 71 and is implanted in the tissue, wherein a cable 76 provides communication with a control unit 73. Preferably, anode 74 is far from cuff 71, for example, in the chest area. Additionally, anode 74 may be integrated with control unit 73, in which case cable 76 need not be used.

Control unit 73 preferably includes power source 20, transceiver 22, controller 24, and pulse generator 26. Controller 24 activates pulse generator 26, for driving electrode configurations 15, via a cable 79, which leads to cables 21 and 76.

The asymmetry formed by the positioning of cathode 72 in cuff 71 causes a primary or forward stimulus signal current to be correspondingly greater than a secondary or reverse current. Thus, stimuli generated by electrode configuration 15 of the present embodiment will travel substantially unidirectionally, from arrest end 75 towards escape end 77.

It will be appreciated that other monopolar unidirectional electrode configurations are possible and are within the scope of the present invention.

Referring further to the drawings, FIGS. 4A and 4B schematically illustrate an intracorporeal apparatus 80, in accordance with another preferred embodiment of the present invention.

Apparatus 80 includes a cuff 81, comprising two tripolar unidirectional electrode configurations 15, arranged as mirror images to each other. Each unidirectional electrode configuration 15 may be designed, for example, as a cathode 86, an anode 84, and a secondary anode 88, and the mirror image arrangement may be, for example, cathode 86 to cathode 86.

Additionally, each unidirectional electrode configuration 15 of apparatus 80 may be designed according to the teaching of commonly owned US Patent Application 20030050677, to Gross, et al., entitled, "Electrode assembly for nerve control," whose disclosure is incorporated herein by reference. Gross, et al. teach an apparatus for applying current to a nerve, the apparatus being designed to reduce the virtual cathode effect. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site. For most applications, the secondary anodal current is of lower magnitude than the primary anodal current. In this manner, the "virtual cathode" effect induced by the primary anodal current is minimized. As described hereinabove, the virtual cathode effect can stimulate, rather than block, the generation of action potentials in fibers in a region adjacent to the application of anodal current of a sufficiently high magnitude. In accordance with a preferred embodiment of the present invention, application of the primary and secondary anodal currents in appropriate ratios is configured to generally minimize the virtual cathode effect. Typically, but not necessarily, the ratio of the primary to the secondary anodal current ranges from 5:1 to 10:1. Additionally, the apparatus may include a housing to which the cathode and a plurality of anodes are coupled, wherein one of the anodes is positioned within the housing so as to reduce a virtual cathode effect induced by another one of the anodes.

Figure 5:
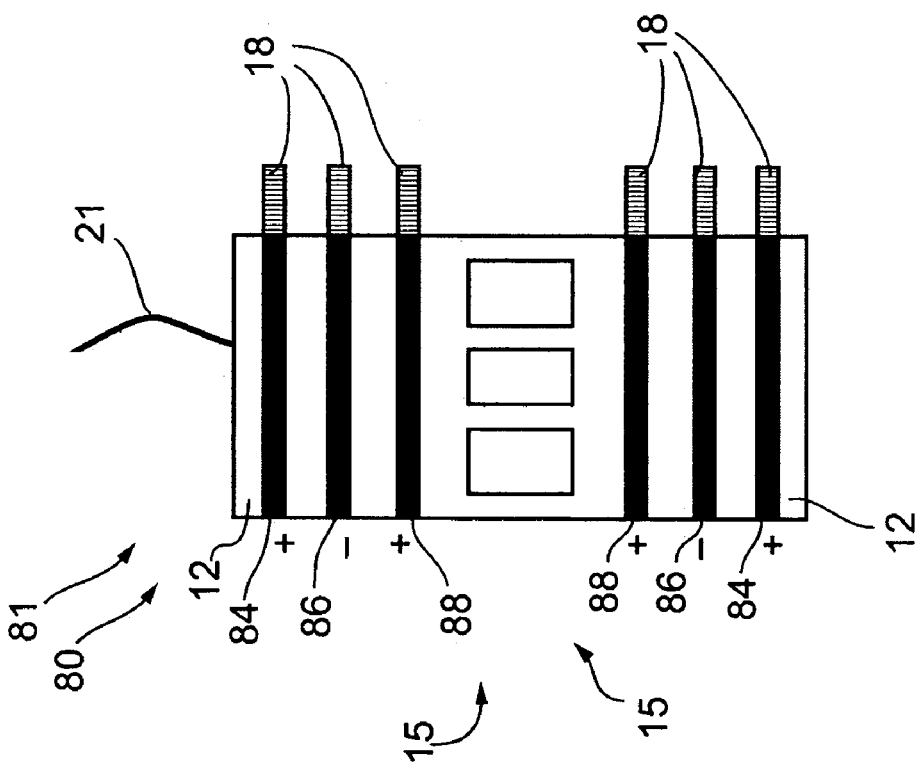
FIG. 5 schematically illustrates an intracorporeal apparatus, for activating, inhibiting, selectively activating, or selectively inhibiting action-potential propagations, in a preselected nerve branch, in accordance with yet another preferred embodiment of the present invention.

Referring further to the drawings, FIG. 5 schematically illustrates an alternative design for apparatus 80, for activating, inhibiting, selectively activating, or selectively inhibiting action-potential propagations, in preselected nerve branch 34, in accordance with yet another preferred embodiment of the present invention.

Accordingly, cathode 86 is flanked by two anodes, 84 and 88, and the mirror image arrangement is secondary anode 88 to secondary anode 88.

It is known in the art that an axon's sensitivity to stimulation increases with its diameter. This sensitivity is both for activation by cathodic stimulation and inhibition by anodic stimulation. In general, nerve stimulation is performed with the cathode. As the current is increased, fibers of lower diameters are "recruited," or stimulated. At a low current, only A fibers are activated, while at a higher current, both A and B fibers are activated. However, when it is desired to activate, for example, only B fibers, the current is divided between the primary and secondary anodes, such that while the cathode operates at a current that activate both A and B fibers, the primary anode inhibits A fibers, by hyper-polarization tuned specifically for these larger-diameter fibers. Thus, an overall activation of B fibers is achieved, with the action potential propagation in the B fibers being towards the secondary anode. In this manner it is possible to predefine a range of nerve-fiber diameters and activate them specifically.

In accordance with the present invention, selective nerve stimulation can be used in conjunction with nerve-branch-specific stimulation to achieve selective stimulation of a specific range of fiber diameters, substantially restricted to a preselected nerve branch.

Examples of applications where selective nerve stimulation is important are as follows:

i. Heart rate control: The heart is innervated only by Vagal B fibers, while A fibers innervate other muscles. Activating A fibers will cause severe side effects such as coughing and voice changes, so it is desired to activate only the B fibers;

ii. Muscle control: B fibers control fine movements, while A fibers produce big contractions.

In the present embodiment, the unidirectional tripolar electrode design is in accordance with the teaching of D. M. Fitzpatrick et al., "A Nerve Cuff Design for the Selective Activation and Blocking of Myelinated Nerve Fibers", Ann. Conf. of the IEEE Eng. in Medicine and Biology Soc., Vol. 13, No. 2, pp. 906, 1991.

As taught by Fitzpatrick et al., the tripolar electrode used for muscle control includes a central cathode flanked on its opposite sides by two anodes. The central cathode generates action potentials in the motor nerve fiber by cathodic stimulation; one anode produces a complete anodal block in one direction so that the action potential produced by the cathode is unidirectional; and the other anode produces a selective anodal block to permit passage of the action potential in the opposite direction through selected motor nerve fibers to produce the desired muscle stimulation or suppression.

It will be appreciated that selective stimulation may also be achieved in accordance with the teaching of J. F. X. Jones, Y. Wang, and D. Jordan (1995): Heart Rate Response to Selective Stimulation of Cardiac Vagal C-Fibers in Anesthetized Cats, Rats, and Rabbits," J. Physiol., 489, 203-214, incorporated herein by reference, which describes the use of two bipolar electrodes to stimulate only a certain group of fibers (for example, only C-fibers), based on their diameters.

Accordingly, an arrangement of four bipolar electrode configurations may be used, two bipolar electrode configurations on proximal side 42, with the unidirectional direction of both being distally, and two bipolar electrode configurations on distal side 44 of nerve junction 35, with the unidirectional direction of both being proximally.

It will be appreciated that selective stimulation may also be achieved in accordance with the teaching of commonly owned U.S. Pat. No. 6,600,954 to Cohen et al., dated Jul. 29, 2003, and entitled, "Method and Apparatus for Selective Control of Nerve Fibers," whose disclosure is incorporated herein by reference. U.S. Pat. No. 6,600,954 describes a method and apparatus particularly useful for pain control by selectively blocking the propagation of body-generated action potentials traveling through a nerve bundle by using a tripolar electrode device to generate unidirectional action potentials to serve as collision blocks with the body-generated action potentials representing pain sensations in the small-diameter sensory fibers. In the described preferred embodiments there are a plurality of electrode devices spaced along the length of the nerve bundle which are sequentially actuated with delays corresponding to the velocity of propagation of the body-generated action potentials through the large-diameter fibers to produce a "green wave" effect which minimizes undesired anodal blocking of the large-diameter fibers while maximizing the collision blocking of the small-diameter fibers.

For example, using the teaching of U.S. Pat. No. 6,600,954, an arrangement of two pluralities of electrode devices may be used, a first plurality on proximal side 42, with its unidirectional direction being distally, and a second plurality on distal side 44 of nerve junction 35, with its unidirectional direction being proximally.

Alternatively, each unidirectional electrode configuration 15 may include a plurality of electrodes, as taught by commonly owned US Patent Application 20030050677, to Gross, et al., entitled, "Electrode assembly for nerve control," describe hereinabove.

Alternatively, each unidirectional electrode configuration 15 may be designed according to the teaching of commonly owned US Patent application 20030045914A1, to Cohen, et al., entitled, "Treatment of disorders by unidirectional nerve stimulation," whose disclosure is incorporated herein by reference. Cohen, et al., teach an apparatus for treating a condition of a subject. An electrode device is adapted to be coupled to longitudinal nervous tissue of the subject, and a control unit is adapted to drive the electrode device to apply to the nervous tissue a current, which is capable of inducing action potentials that propagate in the nervous tissue in a first direction, so as to treat the condition. The control unit is further adapted to suppress action potentials from propagating in the nervous tissue in a second direction opposite to the first direction. For example, the electrodes may be configured to induce efferent nerve impulses (i.e., action potentials propagating in the direction of organ 36), while suppressing afferent nerve impulses traveling towards the brain.

The method of US Patent application 20030045914A1, to Cohen, et al., includes applying a plurality of electrode devices to the nerve bundle, spaced at intervals along the bundle. Each electrode device is capable of inducing, when actuated, unidirectional "electrode-generated" action potentials, which produce collision blocks with respect to the naturally-generated action potentials propagated through the second group of nerve fibers. Moreover, each electrode device is actuated in sequence, with inter-device delays timed to generally match the first conduction velocity and to thereby produce a wave of anodal blocks, which: (a) minimize undesired blocking of the naturally-generated action potentials propagated through the first group of nerve fibers, while (b) maximizing the generation rate of the unidirectional electrode-generated action potentials which produce collision blocks of the naturally-generated action potentials propagated through the second group of nerve fibers. Such a method may be used for producing collision blocks in sensory nerve fibers in order to suppress pain, and also in motor nerve fibers to suppress selected muscular or glandular activities.

It will be appreciated that selective stimulation can be achieved with a monopolar electrode, as taught in conjunction with FIGS. 3A-3C, for example, according to Ungar I. J. et al., "Generation of unidirectionally propagating action potentials using a monopolar electrode cuff," Annals of Biomedical Engineering, 14:437-450 (1986). By using asymmetrical cuff 71, the relative sizes of the virtual anodes near edges 75 and 77 of cuff 71 can be controlled. Adjusting the relative distances of cathode 72 from edges 75 and 77 enables one to get a configuration similar to that of a tripolar electrode and thus achieve selectiveness.

Figure 6:
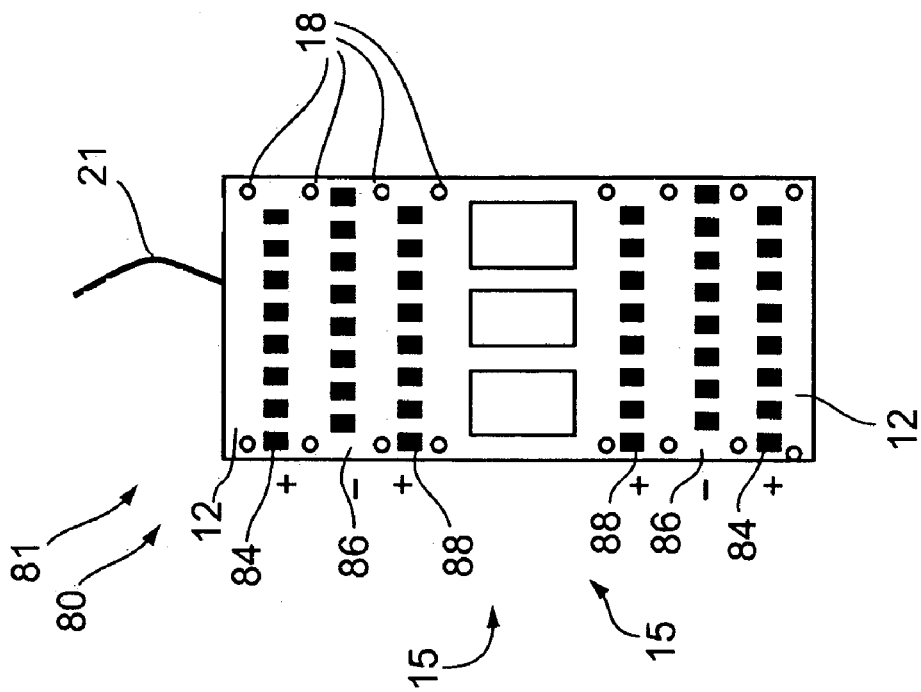
FIG. 6 schematically illustrates an intracorporeal apparatus, for activating, inhibiting, selectively activating, or selectively inhibiting action-potential propagations, in a preselected nerve branch, in accordance with still another preferred embodiment of the present invention.

Referring further to the drawings, FIG. 6 schematically illustrates an alternative design for apparatus 80, for activating, inhibiting, selectively activating, or selectively inhibiting action-potential propagations, in preselected nerve branch 34, in accordance with still another preferred embodiment of the present invention.

In the present embodiment, the electrodes are formed as pads.

Referring further to the drawings, FIGS. 7A-7F schematically illustrate an intracorporeal apparatus for monitoring, activating, inhibiting, selectively activating, or selectively inhibiting action-potential propagations, in a preselected nerve branch, in accordance with yet another preferred embodiment of the present invention.

When no pulse is generated by pulse generator 26 (FIG. 7C), electrode configurations 15 may be operative to sense naturally occurring efferent and afferent action potentials propagating through nerve trunk 32.

As seen in FIG. 7A, afferent action-potential propagations 43, from organ 36, relating for example, to diffused pain, will be sensed by proximal electrode configuration 15A, but not by distal electrode configuration 15B. However, afferent action-potential propagations 45, from an organ more distal than organ 36, will be sensed by both electrode configurations 15A and 15B. By differentiating between the signals sensed by the distal and proximal electrode configurations 15A and 15B, controller 24 may determine when afferent action-potential propagations originate from organ 36.

Conversely, as seen in FIG. 7B, efferent action-potential propagations 47, heading towards organ 36, will be sensed by proximal electrode configuration 15A, with respect to the brain, but not by distal electrode configuration 15B. Yet, efferent action-potential propagations 49, heading towards an organ more distal than organ 36, will be sensed by both electrode configurations 15A and 15B. Again, by differentiating between the signals sensed by the distal and proximal electrode configurations 15A and 15B, controller 24 may determine when efferent action-potential propagations are heading towards organ 36.

It will be appreciated that for sensing action potential associated with organ 36, electrode configurations 15A and 15B need not be unidirectional. Any two electrode configurations, implanted on nerve trunk 32, so as to flank junction 35, may be operative for discriminating between action potentials associated with organ 36 and those associated with more distal organs.

In accordance with the present invention, apparatus 85 is constructed in accordance with any one of the embodiments provided hereinabove. However, in general, some amplification is required for the sensed signals to be properly evaluated.

Thus, as seen in FIG. 7C, control unit 83 preferably includes at least one amplifying component 28, in communication with controller 24. Preferably, cable 21, which provides communication between control unit 83 and cuff 81 splits into a cable 21A, which leads from pulse generator 26 to electrode configurations 15, on cuff 81, and a cable 21B, which leads from electrode configurations 15 to amplifying component 28. In this manner, incoming signals from electrode configurations 15 are amplified before reaching controller 24, for evaluation.

As seen in FIG. 7D, when it is desired to perform selective nerve-branch-specific activation and (or) inhibition, responsive to monitoring by electrode configurations 15A and 15B, a tripolar, unidirectional electrode configuration, for example, as taught by D. M. Fitzpatrick et al., "A Nerve Cuff Design for the Selective Activation and Blocking of Myelinated Nerve Fibers", Ann. Conf. of the IEEE Eng. in Medicine and Biology Soc., Vol. 13, No. 2, pp. 906, 1991, may be used. Alternatively, another electrode configuration, preferably adapted for selective nerve-branch-specific activation and (or) inhibition, may be used.

As seen in FIG. 7E, when monitoring of the nerve trunk takes place, sensor unit 19 need not be used, since activities of organ 36 are sensed through the nerve trunk. It will be appreciated that sensor unit 19 may still be used, when desired.

It will be appreciated that monitoring nerve trunk 32 by electrode configurations 15A and 15B may be used for evaluating the condition of the nerve trunk, as a function of time, for example, for possible effects of electrostimulation.

Figure 7F:
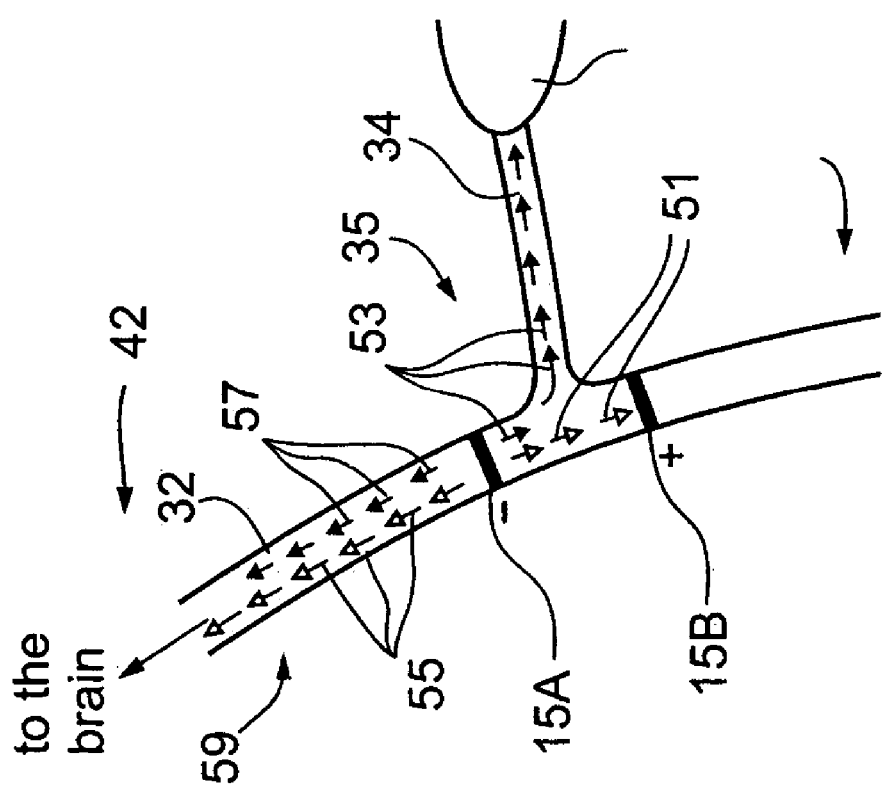

FIG. 7F schematically illustrates an intracorporeal apparatus 59 for activating an action-potential propagation, in preselected nerve branch 34, in accordance with another embodiment of the present invention. Accordingly, proximal electrode configuration 15A is a cathode and distal electrode configuration 15B is an anode. Activation of action potential propagations 51 and 53 takes place by cathode 15A, while inhibition of action potential propagation 51 by local hyperpolarization is performed by anode 15B, to prevent action potential propagation 51 from propagating beyond anode 15B. Nonetheless, action potential propagation 53, which is specific to the nerve fibers leading to organ 36, continues in nerve branch 34, towards organ 36.

It will be appreciated that this embodiment is less preferred for several reasons:

i. proximal electrode configuration 15A also activates action potential propagations 55 and 57, to the brain, and these are not blocked;

ii. the inhibition of action potential propagation 51 by local hyperpolarization by anode 15B must be timed exactly with respect to the activation by cathode 15A; and iii. the anodal block also blocks other naturally occurring action potentials passing through anode 15B.

In accordance with the present invention, the operational modes of the intracorporeal apparatus of FIGS. 1A-7F, may be any one, or a combination of the following:

i. generating efferent action-potential propagations, substantially restricted to preselected nerve branch 34;

ii. inhibiting afferent action-potential propagations, from nerve branch 34;

iii. selectively generating action-potential propagations, in a subset of nerve fibers of a predetermined diameter range, substantially restricted to preselected nerve branch 34;

iv. selectively inhibiting action-potential propagations, in a subset of nerve fibers of a predetermined diameter range, substantially restricted to preselected nerve branch 34;

v. monitoring efferent action-potential propagations, leading to preselected nerve branch 34; and vi. monitoring afferent action-potential propagations, from nerve branch 34.

Figure 8:
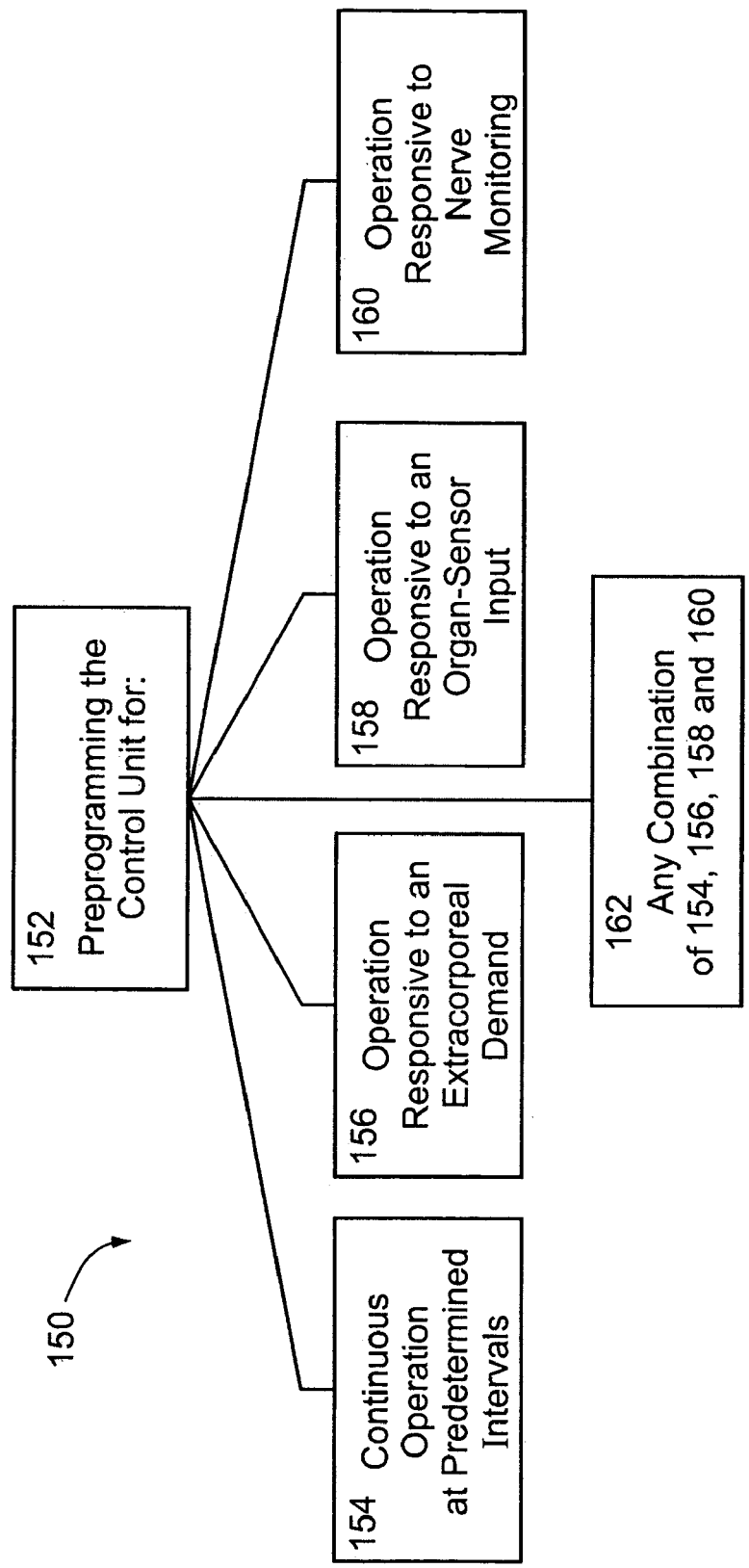
FIG. 8 schematically illustrates modes of operation, in accordance with preferred embodiments of the present invention.

Referring further to the drawings, FIG. 8 schematically illustrates a Flowchart 150, of preprogrammed operational modes of intracorporeal controller 24 (FIGS. 1E, 3C, 7C), in accordance with preferred embodiments of the present invention.

As seen in Box 154, intracorporeal controller 24 may be programmed for continuous operation, at predetermined intervals.

Alternatively, as seen in Box 156, controller 24 may be programmed for operation, responsive to a demand from an extracorporeal station, communicated to transceiver 22 (FIGS. 1E, 3C, 7C), for example, as described hereinbelow, in conjunction with FIGS. 9A-9G. The extracorporeal demand may come from person 50 (FIGS. 1I, 1J, and 7D), from a caretaker (not shown), or from a monitoring call center described hereinbelow in conjunction with FIG. 9G.

Alternatively, as seen in Box 158, controller 24 may be programmed for operation, responsive to input from sensor 17, implanted in organ 36 (FIGS. 1H-1J).

Alternatively, as seen in Box 160, controller 24 may be programmed for operation, responsive to the monitoring of electrode configurations 15A and 15B (FIGS. 7A-7D).

As seen in Box 162, a combination of the above may be employed.

Referring further to the drawings, FIGS. 9A-9G schematically illustrate various extracorporeal systems 100, adapted for communication with intracorporeal controller 24 (FIGS. 1E, 3C, 7C), via receiver 22 or transceiver 22, and possibly also with each other and (or) with a monitoring call center 130, in accordance with the present invention.

As seen in FIG. 9A, extracorporeal system 100 may be a remote-control unit 90, which may include a display panel 92, control buttons 94, a connector 96 for connection to a computer system, preferably being a USB connector, a transmitter 98, which may further operate as a transceiver 98, preferably, an antenna 91, a power source 93, and preferably also a plug for recharging power source 95. It will be appreciated that a separate receiver may be used. Transceiver 98 may operate by RF, IR and may employ BlueTooth protocol.

Additionally, as seen in FIGS. 9B-9F, extracorporeal system 100 may be a mobile phone (FIG. 9B), a telephone (FIG. 9C), a palmtop or PDA (FIG. 9D), a laptop (FIG. 9E), a computer (FIG. 9F), or another remote system, as known. In general, extracorporeal systems 100 include display panels 92 and control buttons 94.

Communication between extracorporeal systems 100 may be performed via connectors and cables, for example, via USB connectors, or by telephone, or in a wireless manner, by RF or IR waves, for example, using BlueTooth protocol.

Additionally, extracorporeal system 100 may further communicate with monitoring call center 130 (FIG. 9G), for example, by phone, or by mobile phone. Monitoring call center 130 may be a clinic, a heath center, or another monitoring center, as applicable, for overseeing, monitoring, and evaluating the operation of apparatus 10, 40, 70, 80 and (or) 85. Preferably, monitoring call center 130 includes an attendant 136, such as a medical practitioner, a nurse, a social worker, and (or) another attendant, as applicable, a computer system 132, and a telephone or cell phone 134. Monitoring call center 130 may also be a center-on-the-go, for example, of medical practitioner 136, his laptop 132, and his cell phone 134.

Communication may include:
1. information from sensor unit 19 (FIG. 1H) or apparatus 85 (FIG. 7A-7D) to extracorporeal system 100, and from it, possibly also to monitoring call center 130; and
2. instructions from extracorporeal system 100, or possibly also from monitoring call center 130, via extracorporeal system 100, to intracorporeal controller 24 (FIGS. 1E, 3C, 7C), for example, to monitor, activate, inhibit, and (or) selectively activate action-potential propagations, of a specified current, frequency, and waveform, to discontinue monitoring, activating, inhibiting, and (or) selectively activating, or to change certain operational parameters.

It will be appreciated that processing of signals from sensor unit 19 (FIG. 1H) or apparatus 85 (FIG. 7A-7D) may be performed by intracorporeal controller 24 (FIGS. 1E, 3C, 7C), by extracorporeal system 100, or by monitoring call center 130 (FIG. 9G).

It will be appreciated that any one of extracorporeal systems 100 may be designed as a telephone or a cell phone with specific codes for quick and easy communication both with monitoring call center 130 and with intracorporeal controller 24 (FIGS. 1E, 3C, 7C). For example, dialing *10 may reach medical attendant 136 at monitoring call center 130, dialing *11 may reach computer system 132 at monitoring call center 130, dialing *12 may communicate with intracorporeal controller 24 (FIGS. 1E, 3C, 7C) and initiate activation.

Figure 10:
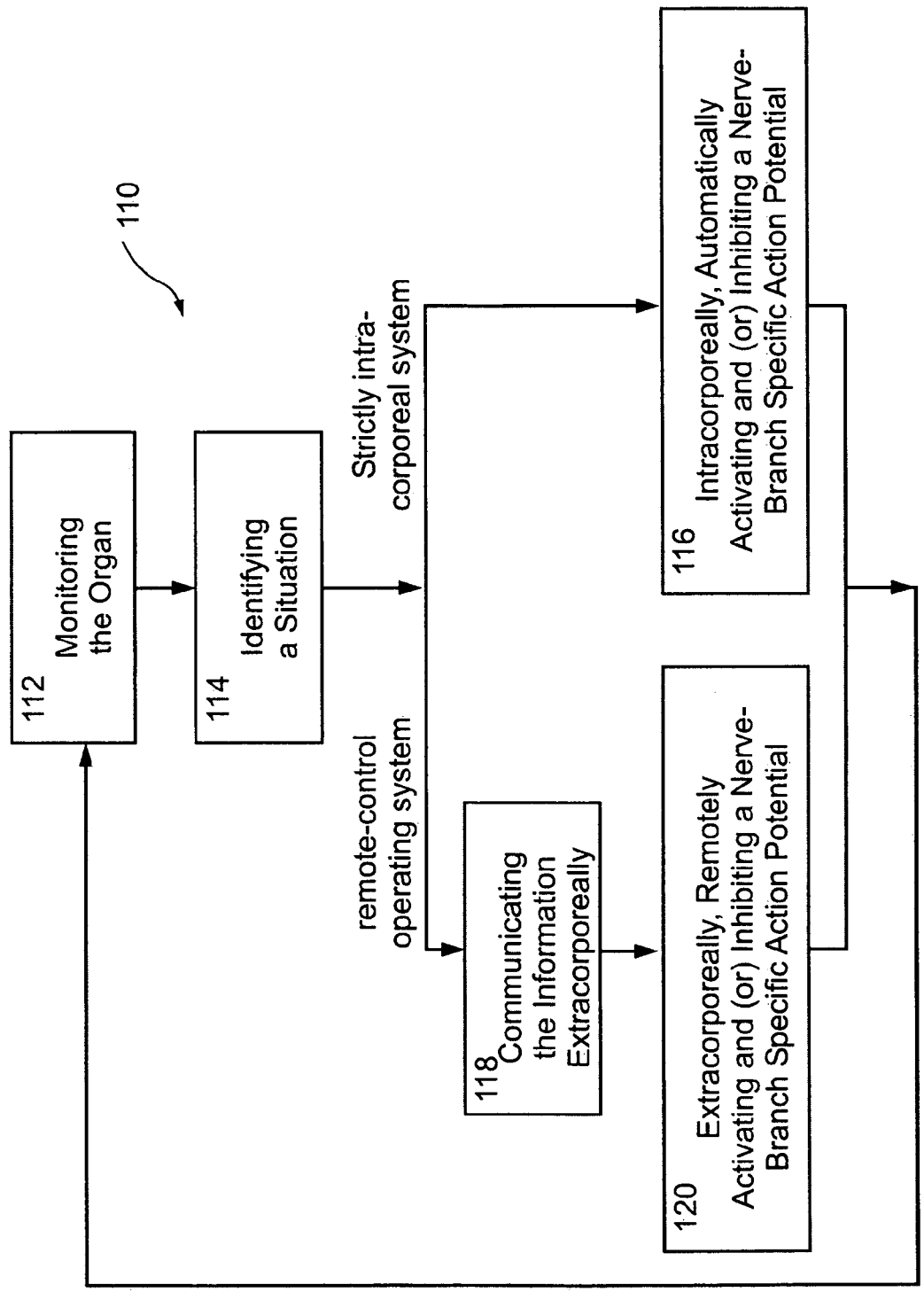
FIG. 10 schematically illustrates a closed-loop operational Flowchart, for activating, inhibiting, selectively activating, or selectively inhibiting action-potential propagations, in a preselected nerve branch, in accordance with a preferred embodiment of the present invention.

Referring further to the drawings, FIG. 10 schematically illustrates a closed-loop operational Flowchart 110, for activating, inhibiting, selectively activating, or selectively inhibiting action-potential propagations, in preselected nerve branch 34, in accordance with a preferred embodiment of the present invention.

As seen in Box 112, sensor unit 19 monitors organ 36.

As seen in Box 114, a situation calling for action is identified.

For a strictly intracorporeal system, seen in Box 116, intracorporeal controller 24 (FIGS. 1E, 3C, 7C) will activate, inhibit, or selectively activate action-potential propagations, substantially only in preselected nerve branch 34, responsive to the situation of Box 114.

For a remote-control operated system, as seen in Box 118, information about the situation of Box 114 is communicated to extracorporeal station 100 and possibly also to monitoring call center 130, via extracorporeal system 100.

As seen in Box 120, extracorporeal system 100, or monitoring call center 130, via extracorporeal system 100, will activate, inhibit, or selectively activate action-potential propagations, substantially only in preselected nerve branch 34, responsive to the situation of Box 114.

Figure 11:
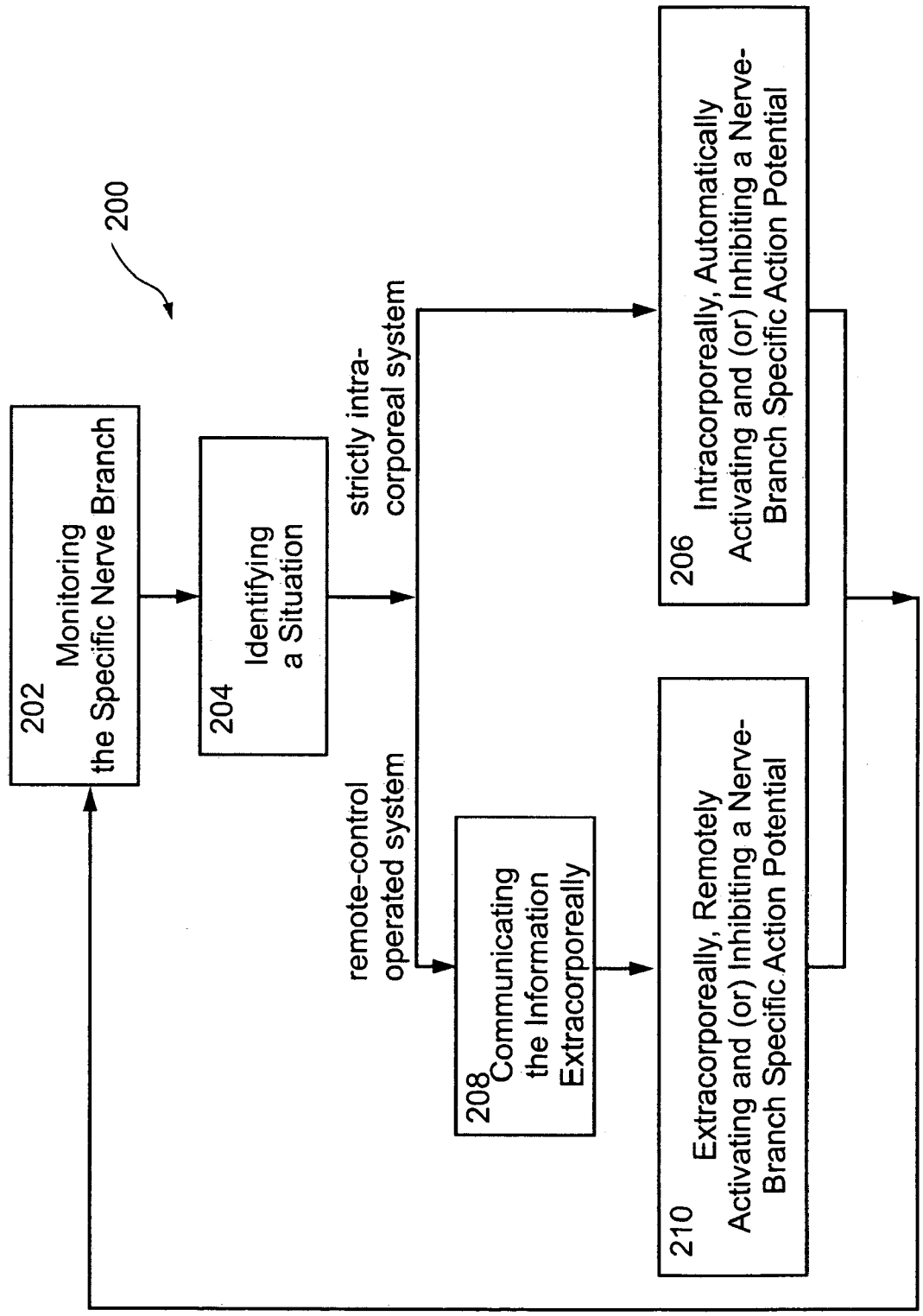
FIG. 11 schematically illustrates a closed-loop operational Flowchart, for activating, inhibiting, selectively activating, or selectively inhibiting action-potential propagations, in a preselected nerve branch, in accordance with another preferred embodiment of the present invention.

Referring further to the drawings, FIG. 11 schematically illustrates a closed-loop operational Flowchart 200, for activating, inhibiting, selectively activating, or selectively inhibiting action-potential propagations, in preselected nerve branch 34, in accordance with another preferred embodiment of the present invention.

As seen in Box 202, apparatus 85 monitors preselected nerve branch 34, via action potentials passing through electrode configurations 15A and 15B on nerve trunk 32.

As seen in Box 204, a situation calling for action is identified.

For a strictly intracorporeal system, seen in Box 206, intracorporeal controller 24 (FIGS. 1E, 3C, 7C) will activate, inhibit, or selectively activate action-potential propagations, substantially only in preselected nerve branch 34, responsive to the situation of Box 204.

For a remote-control operated system, as seen in Box 208, information about the situation of Box 204 is communicated to extracorporeal station 100 and possibly also to monitoring call center 130, via extracorporeal system 100.

As seen in Box 210, extracorporeal system 100, or monitoring call center 130, via extracorporeal system 100, will activate, inhibit, or selectively activate action-potential propagations, substantially only in preselected nerve branch 34, responsive to the situation of Box 204.

Figures 12A, 12B:
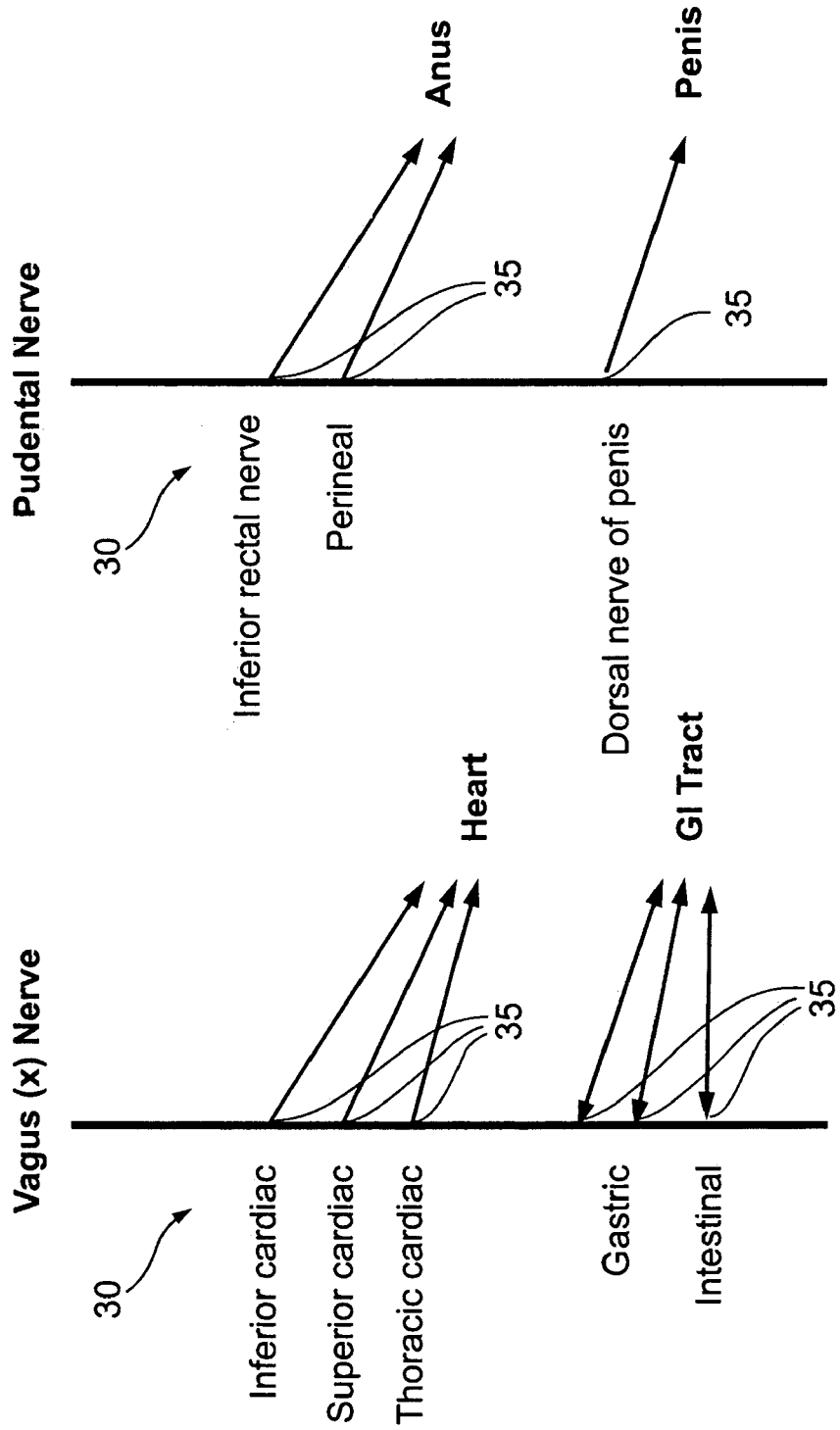
FIGS. 12A and 12B schematically illustrate nerve junctions, at which nerve-branch-specific monitoring, activating, inhibiting, and (or) selectively activating may be applied, in accordance with the present invention.

Referring further to the drawings, FIGS. 12A and 12B schematically illustrate nerve junctions, at which nerve-branch-specific monitoring, activating, inhibiting, and (or) selectively activating may be applied, in accordance with the present invention.

The junctions include the Vagus nerve and its related branches and the Pudental nerve and its related branches. Arrows in both directions indicate that a particular branch may be either activated or inhibited. Arrows in the direction of an organ only, indicate that only activation is important.

Table 1 provides examples of the types of nerve activation and inhibition that may be applied, in accordance with the present invention. It will be appreciated that monitoring, activating, inhibiting, and (or) selectively activating may be applied to other nerve structures and junctions as well.

TABLE 1

| Nerve Trunk | Nerve Branch | Activate | Block | Application | Sensory Input |
|---|---|---|---|---|---|
| Vagus | Superior cardiac | √ | | decrease heart rate, for heart failure patients | heart-rate sensor, to indicate HR |
| Vagus | Inferior cardiac | √ | | decrease heart rate, for heart failure patients | heart-rate sensor, to indicate HR |
| Vagus | Thoracic cardiac | √ | | decrease heart rate, for heart failure patients | heart-rate sensor, to indicate HR |
| Vagus | Gastric | √ | | Increase gastric motility locally, Treat gastric atonia, Stop nausea, vomiting | Patient request Gastric Acidity Esophageal contractions |
| Vagus | Gastric | | √ | Reduce appetite Treat dyspepsia | Patient request |
| Vagus | Intestine | √ | | Increase intestinal motility locally, Treat intestinal atonia Treat constipation Treat Irritable bowel syndrome | Patient request Time of day |
| Vagus | Intestine | | √ | stop nausea, vomiting Treat Irritable bowel syndrome | Patient request Time of day |
| Pudental | inferior rectal | √ | | treat fecal incontinence | Rectal pressure Abdominal Pressure |
| Pudental | perineal nerve | √ | | treat fecal incontinence | Rectal pressure Abdominal Pressure |
| Pudental | Dorsal nerve of penis | √ | | cause erection to treat impotence | Patient request |

It is expected that during the life of this patent many relevant apparatus and methods for nerve-branch specific monitoring, activating, inhibiting, and (or) selectively activating will be developed and the scope of the present invention is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus comprising:
   a dual electrode arrangement, which comprises:
      a proximal electrode configuration, adapted to be implanted on a nerve trunk, on a proximal side, with respect to the brain, of a junction of said nerve trunk with a preselected nerve branch, so as to communicate with:
         i. first nerve fibers of said nerve trunk, which at said junction remain with said nerve trunk, and
         ii. second nerve fibers of said nerve trunk that branch into said preselected nerve branch; and
      a distal electrode configuration, adapted to be implanted on said nerve trunk, on a distal side of said junction, so as to communicate with said first nerve fibers and not with said second nerve fibers; and
   an electronic unit, in signal communication with both said proximal and distal electrode configurations, said electronic unit being configured to generate efferent action-potential propagations substantially restricted to said second nerve fibers, by:
      driving said proximal electrode configuration to generate distally moving action potential propagations along said first and second nerve fibers, and
      driving said distal electrode configuration to generate proximally moving action potential propagations along said first nerve fibers, such that said distally and proximally moving action potential propagations along said first nerve fibers collide and block each other, while said distally moving action potential propagations along said second nerve fibers propagate into said preselected nerve branch.

2. The apparatus of claim 1, wherein said electronic unit comprises a controller.

3. The apparatus of claim 2, further comprising a sensor unit, in communication with said controller.

4. The apparatus of claim 1, wherein said electronic unit comprises a pulse generator.

5. The apparatus of claim 1, wherein said electronic unit comprises an amplification component.

6. The apparatus of claim 1, further comprising an extracorporeal station, wherein said electronic unit comprises a receiver, configured for remote communication with said extracorporeal station, for receiving instructions from said extracorporeal station.

7. The apparatus of claim 1, further comprising an extracorporeal station, wherein said electronic unit comprises a transmitter, configured for remote communication with said extracorporeal station, for sending data to said extracorporeal station.

8. The apparatus of claim 1, wherein said proximal and distal electrode configurations are configured as unidirectional electrode configurations, each adapted for generating an action-potential propagations substantially in one direction, said unidirectional electrode configurations being arranged as mirror images to each other, such that said distally and proximally moving action potentials propagate towards each other.

9. The apparatus of claim 8, wherein said unidirectional electrode configurations are configured as monopolar, unidirectional electrode configurations.

10. The apparatus of claim 8, wherein said unidirectional electrode configurations are configured as multipolar, unidirectional electrode configurations.

11. The apparatus of claim 10, wherein said unidirectional electrode configurations are configured as bipolar, unidirectional electrode configurations.

12. The apparatus of claim 10, wherein said unidirectional electrode configurations are configured as tripolar, unidirectional electrode configurations.

13. The apparatus of claim 1, wherein said proximal and distal electrode configurations comprise electrodes, having metal surfaces on a side facing said nerve trunk, and spacers, arranged between said electrodes, formed of an electrically insulating material, and having a thickness which is greater than that of the electrodes', for forming a clearance between said electrodes and said nerve trunk, and preventing direct contact between said metal surfaces and said nerve trunk.

14. The apparatus of claim 1, wherein said electronic unit is configured to drive said proximal and distal electrode configurations to generate said distally and proximally moving action potential propagations, respectively, by applying respective currents having respective amplitudes each of which is no greater than 20 mA.

15. The apparatus of claim 1, wherein said proximal and distal electrode configurations are configured as unidirectional electrode configurations, each adapted for generating action-potential propagations substantially in one direction, and wherein said proximal and distal electrode configurations are arranged such that said distally and proximally moving action potentials propagate towards each other.

16. The apparatus of claim 1, wherein:
   said dual electrode arrangement further comprises a cuff, constructed for mounting on said nerve trunk; and
   said proximal and distal electrode configurations are integrated into said cuff, and positioned so as to flank said preselected nerve branch from said proximal and distal sides, respectively, when said cuff is mounted on said nerve trunk.

17. The apparatus of claim 1, wherein said electronic unit is configured to drive said proximal electrode configuration to selectively generate said distally moving action-potential propagations in a first subset of said first nerve fibers and in a second subset of said second nerve fibers having a predetermined diameter range.

18. The apparatus of claim 17, wherein said electronic unit is configured to
drive said distal electrode configuration to selectively generate said proximally moving action potential propagations in said first subset of said first nerve fibers along said first nerve fibers,
such that said distally moving and proximally moving action potential propagations collide and block each other along said first subset of said first nerve fibers,
while said distally moving action potential propagations continue along said second subset of said second nerve fibers.

19. The apparatus of claim 1, further comprising a physiological sensor, in communication with said electronic unit.

20. The apparatus of claim 19, wherein said physiological sensor is selected from the group consisting of: a heart-rate sensor, an electrocardiograph (EKG) sensor, an acid sensor, a tensile sensor, and a blood flow rate sensor.

21. The apparatus of claim 1, wherein said electronic unit is configured to drive said proximal electrode configuration to generate said distally moving action potential propagations substantially without generating action potential propagations moving in a proximal direction.

22. The apparatus of claim 1, wherein said electronic unit is configured to drive said distal electrode configuration to generate said proximally moving action potential propagations substantially without generating action potential propagations moving in a distal direction.

23. The apparatus of claim 1, wherein said electronic unit is configured to activate said proximal and distal electrode configurations simultaneously.

24. A method comprising:
providing a proximal electrode configuration, on a nerve trunk, on a proximal side, with respect to the brain, of a junction of said nerve trunk with a preselected nerve branch, so as to communicate with:
i. first nerve fibers of said nerve trunk, which at said junction remain with said nerve trunk, and
ii. second nerve fibers of said nerve trunk that branch into said preselected nerve branch;
providing a distal electrode configuration, on said nerve trunk, on a distal side of said junction, so as to communicate with said first nerve fibers and not with said second nerve fibers;
providing an electronic unit, in signal communication with said proximal and distal electrode configurations; and
generating efferent action-potential propagations, substantially restricted to said second nerve fibers, of said preselected nerve branch, by:
generating, by said proximal electrode configuration, distally moving action potential propagations along said first and second nerve fibers, and
generating, by said distal electrode configuration, proximally moving action potential propagations along said first nerve fibers, such that said distally and proximally moving action potential propagations along said first nerve fibers collide and block each other, while said distally moving action potential propagations along said second nerve fibers propagate into said preselected nerve branch.

25. The method of claim 24, wherein providing said proximal and distal electrode configurations comprises providing respective unidirectional electrode configurations, each adapted for generating an action-potential propagation substantially in one direction, and wherein providing said proximal and distal electrode configurations comprises arranging said unidirectional proximal and distal electrode configurations as mirror images to each other, such that said distally and proximally moving action potentials propagate towards each other.

26. The method of claim 25, wherein providing said proximal and distal electrode configurations comprises providing respective monopolar, unidirectional electrode configurations.

27. The method of claim 25, wherein providing said proximal and distal electrode configurations comprises providing respective bipolar, unidirectional electrode configurations.

28. The method of claim 27, wherein providing said proximal and distal electrode configurations comprises providing respective tripolar, unidirectional electrode configurations.

29. The method of claim 25, wherein providing said proximal and distal electrode configurations comprises providing respective multipolar, unidirectional electrode configurations.

30. The method of claim 24, wherein generating said distally moving action potential propagations comprises selectively generating, by said proximal electrode configuration, said distally moving action-potential propagations in a first subset of said first nerve fibers and in a second subset of said second nerve fibers having a predetermined diameter range.

31. The method of claim 24, wherein generating said efferent action-potential propagations comprises activating said proximal and distal electrode configurations in accordance with a predetermined schedule.

32. The method of claim 24, wherein generating said efferent action-potential propagations comprises activating said proximal and distal electrode configurations simultaneously.

33. The method of claim 24, wherein providing said proximal and distal electrode configurations comprises providing respective unidirectional electrode configurations, each adapted for generating action-potential propagations substantially in one direction, and wherein providing said proximal and distal electrode configurations comprises arranging said unidirectional proximal and distal electrode configurations such that said distally and proximally moving action potentials propagate towards each other.

34. The method of claim 30, wherein generating said distally moving action potential propagations comprises:
selectively generating, by said distal electrode configuration, said proximally moving action potential propagations in said first subset of said first nerve fibers along said first nerve fibers,
such that said distally moving and proximally moving action potential propagations collide and block each other along said first subset of said first nerve fibers,
while said distally moving action potential propagations continue along said second subset of said second nerve fibers.

35. The method of claim 24, wherein generating, by said proximal electrode configuration, said distally moving action potential propagations comprises generating said distally moving action potential propagations substantially without generating action potential propagations moving in a proximal direction.

36. The method of claim 24, wherein generating, by said distal electrode configuration, said proximally moving action potential propagations comprises generating said proximally moving action potential propagations substantially without generating action potential propagations moving in a distal direction.

37. The method of claim 24, wherein generating said distally and proximally moving action potential propagations comprises applying respective currents having respective amplitudes each of which is no greater than 20 mA.

38. A method for generating efferent action potential propagations substantially restricted to a preselected nerve branch that branches from a nerve trunk at a junction, said nerve trunk including first nerve fibers that do not branch into said nerve branch, and second nerve fibers that branch into said nerve branch, said method comprising:
  applying first and second currents at first and second sites on proximal and distal sides, with respect to a brain, of said junction, respectively; and
  generating said efferent action potential propagations substantially restricted to said nerve branch by:
  configuring said first current to generate distally moving action potential propagations along said first and second nerve fibers, and
  configuring said second current to generate proximally moving action potential propagations along said first nerve fibers, such that said distally and proximally moving action potential propagations along said first nerve fibers collide and block each other, while said distally moving action potential propagations along said second nerve fibers propagate into said nerve branch.

39. The method of claim 38, wherein configuring said first current comprises configuring said first current to selectively generate said distally moving action potential propagations in a first subset of said first nerve fibers and in a second subset of said second nerve fibers having a predetermined diameter range.

40. The method of claim 39, wherein configuring said second current comprises configuring said second current to generate said proximally moving action potential propagations in said first subset of said first nerve fibers along said first nerve fibers, such that said distally moving and proximally moving action potential propagations collide and block each other along said first subset of said first nerve fibers, while said distally moving action potential propagations along said second subset of said second nerve fibers propagate into said nerve branch.

41. The method of claim 38, wherein applying said first and second currents comprises applying said first and second currents simultaneously.

42. The method of claim 38, wherein configuring said first current comprises configuring said first current to generate said distally moving action potential propagations substantially without generating action potential propagations moving in a proximal direction.

43. The method of claim 38, wherein configuring said second current comprises configuring said second current to generate said proximally moving action potential propagations substantially without generating action potential propagations moving in a distal direction.

44. The method of claim 38, wherein the nerve trunk includes a vagus nerve, and wherein generating said efferent action potential propagations comprises generating said efferent action potential propagations substantially restricted to said nerve branch that branches from said vagus nerve.

45. The method of claim 44, wherein said preselected nerve branch is selected from the group consisting of: a superior cardiac branch of said vagus nerve, an inferior cardiac branch of said vagus nerve, and a thoracic cardiac branch of said vagus nerve, and wherein generating said efferent action potential propagations comprises generating said efferent action potential propagations substantially restricted to said selected nerve branch.

46. The method of claim 44, wherein said preselected nerve branch is selected from the group consisting of: a gastric branch of said vagus nerve, and an intestinal branch of said vagus nerve, and wherein generating said efferent action potential propagations comprises generating said efferent action potential propagations substantially restricted to said selected nerve branch.

47. The method of claim 38, wherein the nerve trunk includes a pudendal nerve, and wherein generating said efferent action potential propagations comprises generating said efferent action potential propagations substantially restricted to said nerve branch that branches from said pudendal nerve.

48. The method of claim 47, wherein said preselected nerve branch is selected from the group consisting of: an inferior rectal branch of said pudendal nerve, and a perineal branch of said pudendal nerve, and wherein generating said efferent action potential propagations comprises generating said efferent action potential propagations substantially restricted to said selected nerve branch.

49. The method of claim 48, wherein generating said efferent action potential propagations comprises treating fecal incontinence.

50. The method of claim 47, wherein said preselected nerve branch includes a dorsal nerve of a penis, and wherein generating said efferent action potential propagations comprises generating said efferent action potential propagations substantially restricted to said dorsal nerve.

* * * * *